United States Patent
Chittiboyina et al.

(10) Patent No.: US 10,261,017 B2
(45) Date of Patent: Apr. 16, 2019

(54) METHODS FOR DETECTING AND CATEGORIZING SKIN SENSITIZERS

(71) Applicant: University of Mississippi, University, MS (US)

(72) Inventors: Amar G. Chittiboyina, Oxford, MS (US); Ikhlas Ahmad Khan, Oxford, MS (US); Cristina Avonto, Oxford, MS (US)

(73) Assignee: University of Mississippi, University, MS (US)

( * ) Notice: Subject to any disclaimer, the term of this patent is extended or adjusted under 35 U.S.C. 154(b) by 292 days.

(21) Appl. No.: 15/318,938

(22) PCT Filed: Jun. 26, 2015

(86) PCT No.: PCT/US2015/038142
§ 371 (c)(1),
(2) Date: Dec. 14, 2016

(87) PCT Pub. No.: WO2015/200870
PCT Pub. Date: Dec. 30, 2015

(65) Prior Publication Data
US 2017/0131207 A1 May 11, 2017

Related U.S. Application Data

(60) Provisional application No. 62/017,586, filed on Jun. 26, 2014.

(51) Int. Cl.
*G01N 21/25* (2006.01)
*G01N 21/64* (2006.01)
(Continued)

(52) U.S. Cl.
CPC .......... *G01N 21/6428* (2013.01); *A61B 5/00* (2013.01); *A61K 49/0006* (2013.01);
(Continued)

(58) Field of Classification Search
CPC .......... A61B 5/00; A61B 5/055; A61B 5/441; A61K 49/0006; A61K 49/10; G01N 21/25; G01N 21/6428; G01N 24/08; G01R 33/46
See application file for complete search history.

(56) References Cited

U.S. PATENT DOCUMENTS

| | | |
|---|---|---|
| 2008/0191149 A1 | 8/2008 | Zimenkov et al. |
| 2013/0017616 A1* | 1/2013 | Hudson ............ A61K 31/4415 436/96 |
| 2014/0110881 A1 | 4/2014 | Keledjian et al. |

FOREIGN PATENT DOCUMENTS

| | | | |
|---|---|---|---|
| JP | 2009-186253 A | | 8/2009 |
| JP | 2009186253 A | * | 8/2009 |

(Continued)

OTHER PUBLICATIONS

Chipinda et al. Rapid and Simple Kinetics Screening Assay for Electrophilic Dermal Sensitizers using Nitrobenzenethiol. Chemical Research in Toxicology, 2010,23(5): 918-925. (Year: 2010).*

(Continued)

*Primary Examiner* — Jennifer Wecker
(74) *Attorney, Agent, or Firm* — Stites & Harbison PLLC; Mandy Wilson Decker

(57) ABSTRACT

Methods for detecting skin sensitization chemical compounds using Nuclear Magnetic Resonance (NMR) spectroscopy and/or a microplate spectrophotometric assay or other spectroscopic methods. The presently disclosed subject matter relates to a method of detecting skin sensitization potential of a test chemical compound using Nuclear Magnetic Resonance (NMR) spectroscopy, microplate spectrophotometry or other spectroscopic methods as stand-alone or in combination.

19 Claims, 15 Drawing Sheets

(51) Int. Cl.
| | |
|---|---|
| G01N 21/75 | (2006.01) |
| A61B 5/00 | (2006.01) |
| A61K 49/00 | (2006.01) |
| A61K 49/10 | (2006.01) |
| G01N 24/08 | (2006.01) |
| G01N 21/27 | (2006.01) |
| A61B 5/055 | (2006.01) |
| G01R 33/46 | (2006.01) |

(52) U.S. Cl.
CPC ............ A61K 49/10 (2013.01); G01N 21/25 (2013.01); G01N 21/75 (2013.01); G01N 24/08 (2013.01); A61B 5/055 (2013.01); A61B 5/441 (2013.01); G01N 21/274 (2013.01); G01R 33/46 (2013.01)

(56) References Cited

FOREIGN PATENT DOCUMENTS

| | | |
|---|---|---|
| WO | WO 99/31506 A1 | 6/1999 |
| WO | WO2004092739 A1 | 10/2004 |
| WO | WO2014204990 A2 | 12/2014 |

OTHER PUBLICATIONS

Aleksic et al. Reactivity Profiling: Covalent Modification of Single Nucleophile Peptides for Skin Sensitization Risk Assessment. Toxicological Sciences 1 08(2): 401-411, 2009.
Chipinda et al. Rapid and Simple Kinetics Screening Assay for Electrophilic Dermal Sensitizers using Nitrobenzenethiol. Chemical Research in Toxicology, 2010, 23(5): 918-925.
Chittiboyina et al. Alternative Testing Methods for Skin Sensitization: NMR Spectroscopy for Probing the Reactivity and Classification of Potential Skin Sensitizers, Chemical Research in Toxicology. Jul. 30, 2015.
Ahlfors, S., Sterner, 0., and Hansson, C. (2003) Reactivity of contact allergenic haptens to amino acid residues in a model carrier peptide, and characterization of fonned peptide-hapten adducts. Skin Pharmacol Appl Skin Physiol 16, 59-68.
Gerberick, F., Aleksic, M., Basketter, D., Casati, S., Karlberg, A. T., Kern, P., Kimber, I., Lepoittevin, J.P., Natsch, A., Ovigne, J. M., Rovida, C., Sakaguchi, H., and Schultz, T. (2008) Chemical reactivity measurement and the predicitve identification of skin sensitisers. The report and recommendations ofECV AM Workshop 64. Altern Lab Anim 36, 215-242.
Gerberick, G., Ryan, C., Kern, P., Deannan, R., Kimber, I., Patlewicz, G., and Basketter, D. (2004) A chemical dataset for evaluation of alternative approaches to skin-sensitization testing. Contact dermatitis 50, 274-288.
Gerberick, G., Vassallo, J., Bailey, R., Chaney, J., Morrall, S., and Lepoittevin, J.-P. (2004) Development of a peptide reactivity assay for screening contact allergens. Toxicol. Sci. 81, 332-343.
OECD. (2015) Test No. 442C: In Chemico Skin Sensitisation. http://www.oecdilibrary.org/environment/test-no-442c-in-chemico-skin-sensitisation_9789264229709-en (Accessed on IOth Jun. 2015), OECD Publishing.
Merckel, F., Bernard, G., Mutschler, J., Gimenez-Arnau, E., Gerberick, G. F., and Lepoittevin, J.P. (2010) Effect of a microemulsion system on hapten-peptide reactivity studies: examples of hydroxycitronellal and citral, fragrance skin sensitizers, with glutathione. Chern Res Toxicol23, 1433-1441.
Merckel, F., Gimenez-Arnau, E., Gerberick, G., and Lepoittevin, J.-P. (2013) In chemico evaluation of pro hapten skin sensitizers: behavior of 2-methoxy-4-(13C)methylphenol in the peroxidase peptide reactivity assay (PPRA) as an alternative to animal testing. Toxicology letters 218, 266-272.
Gerberick, G. F., Troutman, J. A., Foertsch, L. M., Vassallo, J.D., Quijano, M., Dobson, R. L., Goebel, C., and Lepoittevin, J. P. (2009) Investigation of peptide reactivity of pro-hapten skin sensitizers using a peroxidase-peroxide oxidation system. Toxicol. Sci. 112, 164-174.
Troutman, J. A., Foertsch, L. M., Kern, P. S., Dai, H. J., Quijano, M., Dobson, R. L., Lalko, J. F., Lepoittevin, J. P., and Gerberick, G. F. (20 11) The incorporation of lysine into the peroxidase peptide reactivity assay for skin sensitization assessments. Toxicol Sci 122, 422-436.
Natsch, A., Ryan, C. A., Foertsch, L., Emter, R., Jaworska, J., Gerberick, F., and Kern, P. (2013) A dataset on 145 chemicals tested in alternative assays for skin sensitization undergoing prevalidation. J Appl Toxicol33, 1337-1352.
Gerberick, G., Vassallo, J., Foertsch, L., Price, B., Chaney, J., and Lepoittevin, J.-P. (2007) Quantification of chemical peptide reactivity for screening contact allergens: a classification tree model approach. Toxicol. Sci. 97, 417-427.
Natsch, A., and Gfeller, H. (2008) LC-MS-based characterization of the peptide reactivity of chemicals to improve the in vitro prediction of the skin sensitization potential. Toxicol. Sci. 106, 464-478.
Roberts, D., and Natsch, A. (2009) High throughput kinetic profiling approach for covalent binding to peptides: application to skin sensitization potency of Michael acceptor electrophiles. Chern. Res. Toxicol. 22, 592-603.
Yamamoto, Y ,, Tahara, H., Usami, R., Kasahara, T., Jimbo, Y., Hioki, T., Fujita, M., 2015. A novel in chemica method to detect skin sensitizers in highly dilut:d reaction conditions. J. Appl. Toxicol. 35, 1348-1360.
Chipinda, I., Ajibola, R., Morakinyo, M., Ruwona, T., Simoyi, R., and Siegel, P. (2010) Rapid and simple kinetics screening assay for electrophilic dermal sensitizers using nitrobenzenethiol. Chern. Res. Toxicol. 23, 918-925.
Roberts, D. W., and Aptula, A. 0. (2014) Electrophilic Reactivity and Skin Sensitization Potency of SNAr Electrophiles. Chern. Res. Toxicol. 27, 240-246.
Andres, E., Sa-Rocha, V. M., Barrichello, C., Haupt, T., Ellis, G., and Natsch, A. (2013) The sensitivity of the KeratinoSens assay to evaluate plant extracts: a pilot study. Toxicol In Vitro 27, 1220-1225.
Bohme, A., Thaens, D., Paschke, A., and Schiiiirmann, G. (2009) Kinetic glutathione chemoassay to quantify thiol reactivity of organic electrophiles—application to alpha,betaunsaturated ketones, acrylates, and propiolates. Chern. Res. Toxicol. 22, 742-750.
Avonto, C., Chittiboyina, A.G., Rua, D., Khan, I.A., 2015. A fluorescence high throughput screening method for the detection of reactive electrophiles as potential skin sensitizers. Toxicol. Appl. Pharmacal. 289, 177-184.
Avonto; C., Chittiboyina, A. G., Wang, M., Vasquez, Y., Rua, D., Khan, I.A., 2016. In chemica evaluation of tea tree essential oils as skin sensitizers: Impact of the chemical composition on aging and generation of reactive species. Chemical research in toxicology 29, 1108-1117.
Avonto, C., Rua, D., Lasonkar, P.B., Chittiboyina, A.G., Khan, I.A., 2017. Identification of a compound isolated from German chamomile (*Matricaria chamomilla*) with dermal sensitization potential. Toxicology and Applied Pharmacology 318, 16-22.
Chittiboyina, A.G., Avonto, C., Khan, I.A., 2016. What Happens after Activation of Ascaridole? Reactive Compounds and Their Implications for Skin Sensitization. Chemical Research in Toxicology 29, 1488-1492.
Chittiboyina, A.G., Avonto, C., Rua, D., Khan, I.A., 2015. Alternative Testing Methods for Skin Sensitization: NMR Spectroscopy for Probing the Reactivity and Classification of Potential Skin Sensitizers. Chern. Res. Toxicol. 28, 1704-1714.
Dimitrov, S., Detroyer, A., Piroird, C., Gomes, C., Eilstein, J., Pauloin, T., Kuseva, C., Iva nova, H., Popova, 1., Karakolev, Y., Ringeissen, S., Mekenyan, 0., 2016. Accounting for data variability, a key factor in in vivo/in vitro relationships: application to the skin sensitization potency (in vivo LLNA versus in vitro DPRA) example. J. Appl. Toxicol. 36, 1568-1578.
Fujita, M., Yamamoto, Y., Tahara, H., Kasahara, T., Jimbo, Y., Hioki, T., 2014. Development of a prediction method for skin sensitization using novel cysteine and lysine derivatives. J. Pharmacal. Toxicol. Methods 70, 94-105.

(56) References Cited

OTHER PUBLICATIONS

Redeby, T., Nilsson, U., Altamore, T.M., Ilag, L., Ambrosi, A., Broo, K., Borje, A., Karlberg, A.-T., 2010. Specific Adducts Formed through a Radical Reaction between Peptides and Contact Allergenic Hydroperoxides. Chem. Res. Toxicol. 23, 203-210.

Takenouchi, 0., Fukui, S., Okamoto, K., Kurotani, S., Imai, N., Fujishiro, M., Kyotani, D., Kato, V., Kasahara, T., Fujita, M., Toyoda, A., Sekiya, D., Watanabe, S., Seta, H., Hirota, M., Ashikaga, T., Miyazawa, M., 2015. Test battery with the human cell line activation test, direct peptide reactivity assay and DEREK based on a 139 chemical data set for predicting skin sensitizing potential and potency of chemicals. J. Appl. Toxicol. 35, 1318-1332.

Wong, C.L., Lam, A.-L., Smith, M.T., Ghassabian, S., 2016. Evaluation of a high-throughput peptide reactivity to format assay for assessment of the skin sensitization potential of chemicals. Front. Pharmacal. 7, 53/51-53/14.

\* cited by examiner

METHODS FOR DETECTING AND CATEGORIZING SKIN SENSITIZERS

RELATED APPLICATIONS

This application claims priority to U.S. Provisional Application Ser. No. 62/017,586, filed Jun. 26, 2014, the entire disclosures of which are incorporated herein by this reference.

TECHNICAL FIELD

The presently-disclosed subject matter relates to methods for detecting, categorizing potential skin sensitizers using Nuclear Magnetic Resonance (NMR) spectroscopy and/or a microplate spectrophotometry or other spectroscopic methods as standalone or in combination.

INTRODUCTION

Skin sensitization is an important toxicological end-point for the safety evaluation of topically applied drug formulations, cosmetics and other types of personal-care products. So far, only animal based tests approved by the United States Interagency Coordinating Committee on the Validation of Alternative Methods (ICCVAM) and the European Centre for the Validation of Alternative Methods (ECVAM).[1] Animal methods include the Guinea Pig Maximization Test (GPMT),[2] Buehler's Test (BT)[3] and lately, the Local Lymph Node Assay (LLNA)[4,5] are the tests routinely used for safety assessment of the sensitizing potential of chemicals. The large number of sacrificed animals constitutes a major drawback in the use of in vivo methods for hazard identification. Thus, there is an urgent need for non-animal based screening methods for the safety assessment of new ingredients proposed for human health. This necessity has been reinforced by the introduction in the European Union (EU), and soon worldwide, of new regulations requiring a minimal use of animals for toxicological screening purposes. The EU's Directives such as the Registration, Evaluation, Authorization and Restriction of Chemicals (REACh) enacted in 2007 require manufacturing companies and importers to assess the safety of thousands of unverified substances,[6] which will lead to an increase in the number of animal tests needed, with an estimated loss of over 84,000 animals per year.[7] The same Directive imposes the minimal use of animals for risk assessment, which has been subject of intense debate on the controversy of the legislation, in particular with respect to toxicological tests where non-animal models are not available yet.[8]

Skin sensitization is a complex phenomenon involving multifarious factors at a molecular, cellular and tissue-levels. The influence of genetic and external factors such as simultaneous presence of pathogen infections or inflammatory processes or the patient's history makes even more challenging for the development of non-animal methods to assess the sensitization potential. Among the numerous rationales, the measurement of the chemical reactivity of potential sensitizer toward model nucleophiles[9,10] and synthetic peptides[11-14] have been shown to be a promising alternative to animal models. Some of these methods are currently under examination by the European Centre for the Validation of Alternative Methods (ECVAM). The DPRA[12,15] and the ARE-Nrf2 luciferase methods[16,17] have been recently adopted by the Organization for Economic Co-operation and Development (OECD) guidelines for testing health effects of chemicals.[18-20] Other methods under evaluation include the LuSens assay, the Myeloid U937 Skin Sensitization Test (MUSST)[21] and the human Cell Line Activation Test (hCLAT).[22] The classification of allergens accordingly their potency is still an evolving process. The most commonly accepted categorization is classification of chemicals as non-sensitizers, weak, moderate, strong or extreme sensitizers, but a clear distinction among categories is merely empirical (based mostly on statistical analysis of the clinical studies). Thus, the categorization of unknown chemicals or mixtures still remains one of the major gaps, but it is vital for the risk assessment.[1]

Although no specific target has yet been clearly identified, several chemical features, such as low molecular weight, lipophilicity and chemical reactivity are considered essential for a potential sensitizer. The majority of existing methods including currently endorsed methods rely on the use of hydrophilic model nucleophiles to estimate the reactivity potential of lipophilic sensitizers. To improve the solubility of lipophilic allergens in aqueous solutions, Merckel et al.[23] suggested a microemulsion system to avoid conducting these in chemico methods in biphasic mixtures. The majority of proven skin sensitizing chemicals are known to be inherently electrophilic; however, it has been estimated that up to a third are non-electrophilic in nature and therefore require either metabolic (pro-haptens), or abiotic activation such as auto-oxidation (pre-haptens) in order to elicit an immunoresponse. To estimate the sensitization potential of these particular classes of compounds, Gerberick et al.[24] proposed the incorporation of peroxidases in their assays. Some of the major issues encountered with the existing methods consist of the lack of mechanistic information, the large amount of required electrophile and the limited number of samples that can be simultaneously analyzed. Moreover, assessment of test material with undefined mechanistic domains or in the presence of pre- or pro-sensitizers and more than one component has been proved an elusive task with existing methods. Therefore, reliable and reproducible new alternative methods are desirable.

SUMMARY

The presently disclosed subject matter relates to a method of detecting skin sensitization potential of a test chemical compound using Nuclear Magnetic Resonance (NMR) spectroscopy, microplate spectrophotometry or other spectroscopic methods as stand-alone or in combination. For example, the NMR method includes the following steps: mixing a nucleophile with at least one chemical compound, acquiring at least one spectrum of the at least one chemical compound over a time period using NMR spectroscopy, determining the skin sensitization potential of the at least one chemical compound by comparing at least one peak area of the at least one spectrum of the chemical compound with at least one peak area of a reference spectrum, determining whether there is a measurable difference between the peak area of the at least one spectrum of the chemical compound and the at least one peak area of the reference spectrum, and identifying the chemical compound as a sensitizing compound when there is a measurable difference between the peak area of the at least spectrum of the chemical compound and the at least one peak area of the reference spectrum. In some embodiments, the method further includes categorizing the reactivity of the at least one chemical compound based on the resulted electrophile depletion.

Further provided in some embodiments of the presently disclosed subject matter, is a spectrophotometric method of detecting skin sensitization potential of test chemical compounds. The spectrophotometric method includes the following steps: mixing at least one of a fluorescent, a luminescent, a colored and a UV-absorbing nucleophile with at least one compound to form a mixture comprising at least one conjugate, removing an amount of unreacted nucleophile from the mixture, quantifying the response of the at least one conjugate using a spectrophotometer, determining the skin sensitization potential of the at least one compound by comparing the response of at least one conjugate with a reference response, and identifying at least one compound as a sensitizing compound when there is a measurable difference between the response of the conjugate and the response of the reference.

Further provided, in some embodiments, the spectrophotometer is a multidetection microplate reader. In some embodiments, the spectrophotometric response is measured at wavelength ranging from about 200 nm to about 780 nm. In some embodiment, the step of mixing a nucleophile with at least one chemical compound further includes a step of adding a catalyst. In some embodiments, the catalyst concentration is about 1% to about 50% of the nucleophile concentration. In some embodiments, non-limiting examples of the nucleophile include an aromatic/aliphatic-thiol, -alcohol, and -amine. In some embodiments, the nucleophile includes, but not limited to, xanthyls, cyaninyl, napthyl, coumaryl, oxadiazolyl, anthracyl, pyrenyl, dansyl, oxaziyl, acridinyl, flavanyl, arylmethinyl, and tetrapyrrolinyl.

Still further, in some embodiments of the presently disclosed subject matter, test chemical compound is an electrophile. In some embodiments, non-limiting examples of the electrophile comprises a $\alpha,\beta$-unsaturated carbonyl compounds, an aromatic compound, an aliphatic compound, a terpene, a sesquiterpene lactone, a natural product. In some embodiments, non-limiting examples of the test chemical compound include a natural product whole extract, a natural product enriched fraction, a single natural product, a mixture of components derived from botanicals, and a mixture of components derived from fresh plant material. In some embodiments, the test chemical compound comprises a mixture of components derived from essential oil, a mixture of components derived from perfume, a mixture of components derived from personal care products, a mixture of components derived from aromatherapy, a mixture of components derived from a hair care product. In some embodiments, the test chemical compound comprises a mixture of components derived from a synthetic chemical, a reactive intermediate, a mixture of component(s) derived upon chemical activation, a mixture of component(s) derived upon oxidation with peroxynitrite, a mixture of component(s) derived upon incubation with AAPH, a mixture of component(s) derived upon incubation with organic or inorganic peroxide, a mixture of component(s) derived upon air oxidation/aging, a mixture of component(s) derived upon auto-oxidation, a mixture of component(s) derived upon air oxidation, and/or UV exposure and/or thermal degradation. In some embodiments, the test chemical compound comprises a mixture of component(s) derived upon biotic activation, a mixture of component(s) derived upon abiotic activation. In some embodiments, the test chemical compound comprises a mixture of component upon metabolic activation, a mixture of component(s) derived upon microbial transformation, a mixture of component(s) derived from fermentation processes, a mixture of component(s) derived upon prokaryotic or eukaryotic metabolism, a mixture of component(s) derived from exogenous transformation including xenobiotic metabolism, a mixture of component(s) derived from genetically modified organism a mixture of component(s) derived upon activation with oxidative stress inducers. In some embodiments, the test chemical compound comprises a mixture of component(s) derived upon enzymatic activation, a mixture of component(s) derived upon incubation with horseradish peroxidase, a mixture of component(s) derived upon incubation with tyrosinases.

BRIEF DESCRIPTION OF THE DRAWINGS

The presently-disclosed subject matter meets some or all of the above-identified needs, as will become evident to those of ordinary skill in the art after a study of information provided in this document.

The novel features of the subject matter of the present disclosure are set forth with particularity in the following description and in the appended sample claims. A better understanding of the features and advantages of the presently disclosed subject matter will be obtained by reference to the following detailed description that sets forth illustrative embodiments, in which the principles of the disclosure are used, and the accompanying drawings of which:

DESCRIPTION OF EXEMPLARY EMBODIMENTS

Figure 1:
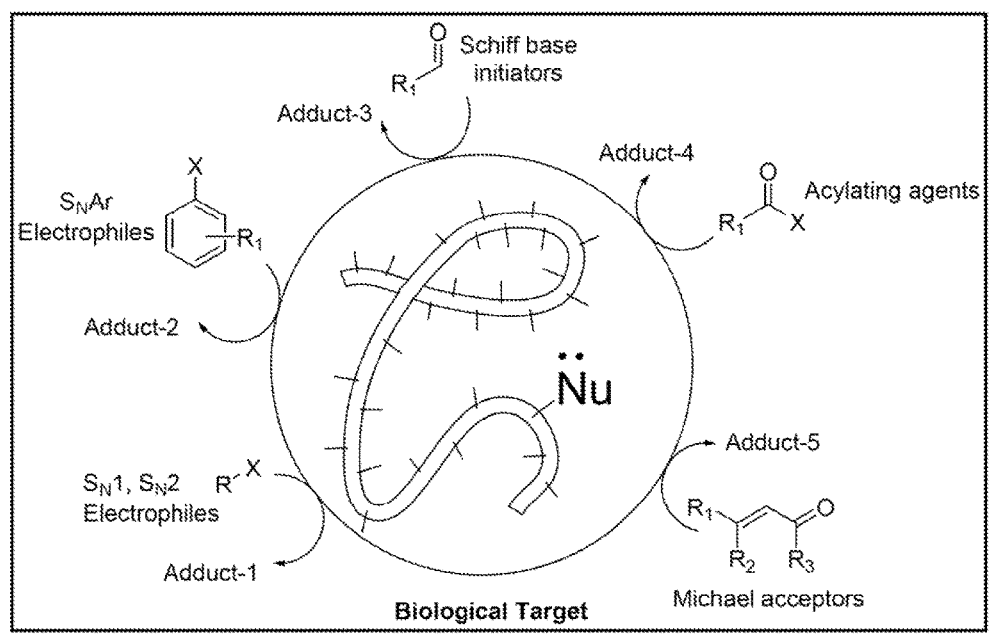
FIG. 1 is a schematic representation of plausible chemical reactions involved in haptenation processes.

The details of one or more embodiments of the presently-disclosed subject matter are set forth in this document. Modifications to embodiments described in this document, and other embodiments, will be evident to those of ordinary skills in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a chemical" includes a plurality of such chemicals, and so forth.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter relates to methods for detecting potential skin sensitizers using Nuclear Magnetic Resonance (NMR) spectroscopy and/or microplate spectrophotometry and/or other spectroscopic methods as standalone or in combination.

Skin sensitization represents the biological event used to classify a more complex immunopathology known as Allergic Contact Dermatitis (ACD). ACD is a common occupational and environmental health problem and the most common form of immunotoxicity in humans.[1] Like many allergic diseases, ACD results from a cascade reaction that involves the hyper-expression of the immuno-response in the epidermal tissue. Allergic contact dermatitis is characterized by two major steps: (i) sensitization and (ii) elicitation. In the first step, contact with a potential chemical allergen (hapten) will stimulate the production of antigens which is responsible for the recruitment and activation of T-lymphocytes. Further contact with the same hapten (elicitation) can result in the production of a vigorous reaction of the immune system, which results in rash, redness and skin lesions with severe outcomes in the worst cases.[25] For toxicological purposes, the sensitization potential of a chemical compound represents the event to be identified, while the elicitation phase is the clinical manifestation of the pathology, and may occur even years after the sensitization step. A potential sensitizer can interact with its biological target though covalent bonding to form an antigenic complex. Reactive amino acid including cysteine, lysine, and, to a lesser extent, arginine, histidine, methionine, and tyrosine residues have been suggested to play a key role in skin sensitization.[26] Although no specific target has yet been clearly identified, several chemical features, such as low molecular weight, lipophilicity and chemical reactivity are considered essential for a potential sensitizer.[27] Because of the nucleophilic nature of the candidate amino acids, many allergenic compounds are highly electrophilic. At present, approximately 4,000 known, low molecular weight allergens have been identified. The majority of these compounds have been classified according to their mechanistic domain.[28] FIG. 1 summarizes the most common mechanistic domains identified for potential skin sensitizers. Many of the strong and moderate sensitizers have been classified as electrophilic $\alpha,\beta$-unsaturated carbonyl compounds.[29-31]

Several molecular targets have been proposed as involved in the regulation of skin sensitization biological pathways. None of these candidates has been found to play a unique role in the pathology so far. It is possible that regulation mechanisms acts as well as external events (such as bacterial infections) contribute to the exacerbation of the sensitization event. Because of this complexity, in vivo models still constitute the most reliable assessment methods. Human volunteer patch tests have been developed,[32] and represent the most reliable predictive method, but for obvious ethical reasons, they cannot be used for hazard identification. Human test are still used to confirm the safety of non-hazardous compounds, but because of the risk of side effects, their use should be undertaken with caution.[33] Major efforts are now focused on the development of alternative test strategies at the cellular and molecular levels for full replacement of animal testing. For example, the human cell line activation tests (h-CLAT)[22, 34] U-937 assay[21] and MUTZ-3[35] are based on phenotypic changes of antigen-presenting cells, including dendritic cells, in response to hapten exposure. The antioxidant response element (ARE) assay[14] and KeratinoSens™[36-38] are based on stimulation of ARE-dependent gene activity in a recombinant cell line.

Interestingly, the first step in the haptenation process is believed to involve covalent binding between the electrophile and the biological target, and many researchers have exploited the concept of "chemical reaction" for the development of alternative in chemico methods. In order to classify potential electrophilic haptens and estimate their potency, several model nucleophiles have been proposed. Schultz et al. introduced the concept of 50% depletion ($RC_{50}$) of reduced glutathione (GSH) in 2 h. Gerberick et al.[12, 13, 39] coined the percent depletion (dp) of GSH or model peptide in 24 h as the reactivity index of a given chemical. The latter method was further modified and improved by Natsch et al.[15] to characterize adduct formations as well as heptapeptide dimerization induced by some skin sensitizers. Later. Roberts and Natsch developed a High-Throughput Kinetic Profiling (HTKP) method[40] and addressed some of the drawbacks associated with peptide reactivity assays. In 2009, an approach using NBD-chloride (4-Chloro-7-Nitrobenzofurazan), fluorogenic glutathione was developed for estimating the skin sensitization potential of a chemical using chromatographic techniques coupled with fluorescent detector.[41-43] This method did not provide structural information nor include the use of the mentioned cysteine reagent for the investigation of potential natural sensitizers or complex mixtures. Alternatively, Chipinda et al.[44] introduced a rapid and simple kinetic screening assay using nitrobenzenethiol and stopped-flow techniques coupled with UV absorbance measurements.

The majority of the immunological literature is directed to lysine-hapten adducts, even though it is well known that several haptens have molecular structures that preferably form adducts with cysteine residues. For example, quinones, add exclusively to the cysteine moiety[9] in the presence of other nucleophilic amino acids in a carrier peptide. Calculation of the $RC_{50}$ (2 h assay), the dp (24 h assay), LC-MS, HTKP and kinetics with nitrobenzenethiol methods serve as promising skin-sensitizing predictive methods. None of these methods provide adequate structural information. Indeed, a common pitfall of the aforementioned methods is the lack of reactivity information, such as the site of reaction when more than one reactive center is present or whether more than one reaction mechanism may apply.[15, 45] Moreover, within the mechanistic domain, the derived classification may not be relevant or biologically significant because of the extreme experimental conditions selected. The majority of the methods mentioned above use a large excess of test electrophile (hapten) (10-200 times excess compared to the tested nucleophile) or long reaction time. Under these conditions (which do not necessary reflect the in vivo dynamics of the sensitization process) a number of side reactions may occur, which could potentially alter the final results of the assay. For classification purposes, the majority of the reported in chemico methods are based on indirect measurement of "thiol depletion," which is hampered by the water solubility of the electrophile, drowning-out effect and air oxidation of test thiol peptide.[46]

Additional complications add up when considering complex, multicomponent formulations as possible skin irritants. A plethora of skincare products and cosmetics are formulated from botanical extracts for the treatment of various dermatological conditions and also to exploit their anti-inflammatory, antiseptic and organoleptic beneficial properties. Classical animal tests, such as the LLNA, normally are only validated for pure preparations, and there is no validation for and little experience with testing mixtures. This is especially true with phytochemicals and complex botanical extracts.[47] Thus it is important to identify skin-sensitizing chemicals and to evaluate their sensitization potential before a complex formulation is introduced in the market.

In some embodiments, the presently disclosed subject matter provides a method for detecting skin sensitization potential of at least one chemical compound using Nuclear Magnetic Resonance (NMR) spectroscopy. The method includes the steps of mixing a nucleophile with at least one chemical compound, acquiring at least one spectrum of the at least one chemical compound over a time period using NMR spectroscopy, determining the reactivity of the at least one chemical compound by comparing at least one peak area of the at least one spectrum of the chemical compound with at least one peak area of a reference spectrum, determining whether there is a measurable difference between the peak area of the at least one spectrum of the chemical compound and the at least one peak area of the reference spectrum, and identifying the chemical compound as a sensitizing compound when there is a measurable difference between the peak area of the at least one spectrum of the chemical compound and the at least one peak area of the reference spectrum. In some embodiments, the method further includes reactivity based categorization of the at least one chemical compound based on the resulted electrophile/nucleophile depletion.

As used herein, the term "reference spectrum" refers to a spectrum to be acquired before initiation of the reaction. For example, it could be a calculated reference spectrum, a reference spectrum taken from a database or a theoretical spectrum. The reference spectrum can also be obtained as the median of a plurality of blank or control spectra.

As used herein the term "reference spectra" refers to an array of multiple reference spectrum acquired for a potential sensitizer.

In some embodiments, non-limiting examples of the nucleophile include an aromatic/aliphatic-thiol, -alcohol and -amine. In some embodiments, the nucleophile is a heteroaromatic, aromatic and aliphatic thiol. Non-limiting examples of a thiol is dansyl cystamine (DCYA), 4-nitrobenzenethiol (NBT), N-acetyl cystamine (NAC), glutathione (GSH). Further non-limiting examples of the nucleophile comprises xanthyls, cyaninyl, napthyl, coumaryl, oxadiazolyl, anthracyl, pyrenyl, oxaziyl, acridinyl, flavanyl, arylmethinyl, tetrapyrrolinyl, dansyl, rhodaminyl, boron-dipyrromethenyl (BODIPY), coumaryl and (7-nitrobenz-2-oxa-1,3-diazolyl (NBD).

In some embodiments, the step of mixing a nucleophile with at least one chemical compound further includes a step of adding a catalyst. Non-limiting examples of the catalyst is 1,5-Diazabicyclo(4.3.0)non-5-ene (DBN), 1,8-Diazabicyclo[5.4.0]undec-7-ene (DBU), dimethylaminopyridine (DMAP), buffer with pH range 7.1-14, triethylamine (TEA) and any organic or inorganic base. In some embodiments, the catalyst concentration is about 1% to about 50% of nucleophile (e.g. DCYA) concentration. In some embodiments, the step of mixing a nucleophile with at least one chemical compound further includes a step of adding a solvent. Non-limiting examples of the solvent includes deuterated form of chloroform, acetonitrile, dimethyl sulfoxide (DMSO), benzene, tetrahydrofuran, water, hexane, pentane, methanol, ethanol, methylene chloride and pyridine. Further, in some embodiments, the step of mixing a nucleophile with at least one chemical compound is in a temperature between about 5° C. to about 65° C. In some embodiments, the stoichiometry of the nucleophile:test chemical is about 1:25 to about 10:1 ratio.

Further provided in some embodiments of the presently disclosed subject matter, is a high throughput spectroscopic method of detecting skin sensitization potential of test chemical compounds. The method includes mixing at least one of a fluorescent, a luminescent, a colored and a UV-absorbing nucleophile with a sensitizing compound to form a mixture comprising a conjugate, removing an amount of unreacted nucleophile from the mixture, and quantifying an amount of the conjugate using a spectrophotometer. For example, the spectrophotometer is a multidetection microplate reader. In some embodiments, the excitation and emission reading points by using the spectrophotometer depends on type of nucleophile used in high throughput spectrophotometric method.

In some embodiments, the step of mixing at least one of a fluorescent, a luminescent, a colored and a UV-absorbing nucleophile with a sensitizing compound further includes a step of adding a solvent. Non-limiting examples of the solvent are acetonitrile, dimethyl formamide (DMF), chloroform, methanol, water, dimethyl sulfoxide, hexane, ethanol, benzene, tetrahydrofuran. In some embodiments, the step of mixing at least one of a fluorescent, a luminescent, a colored and a UV-absorbing nucleophile with a sensitizing compound further includes adding a catalyst. Non-limiting examples of the catalyst include DBN, DBU, and any buffer with pH between 7.1-14.0. In some embodiments, the time for this mixing step is between about 15 minutes to about 180 minutes. In some embodiments, the stoichiometry of nucleophile is about 0.1% to about 100% of test chemical compound. In some embodiment, the step of removing an amount of unreacted nucleophile further includes adding a scavenger. In some embodiments, the scavenger is a functionalized polymer. In some embodiments, the polymer includes any resin capable of scavenging the nucleophilic species.

Additionally, non-limiting examples of the test chemical compound comprises a electrophile, a synthetic chemical, a reactive intermediate, a natural product whole extract, natural product enriched fractions, a single natural product, a mixture of components derived from botanicals, a mixture of components derived from fresh plant material, a mixture of components derived from essential oil, a mixture of components derived from perfume, a mixture of components derived from personal care products, a mixture of components derived from aromatherapy, a mixture of components derived from a hair care product, a synthetic chemical, a mixture of components derived from a synthetic chemical, a mixture of component(s) derived upon metabolic activation, a mixture of component(s) a mixture of component(s) derived upon abiotic activation, a mixture of component(s) derived upon biotic activation, a mixture of component(s) derived upon enzymatic activation, a mixture of component(s) derived upon incubation with human liver microsomes, a mixture of component(s) derived upon incubation with horseradish peroxidase, a mixture of component(s) derived upon incubation with tyrosinases, a mixture of component(s) derived upon microbial transformation, a mixture of component(s) derived from fermentation processes, a mixture of component(s) derived upon prokaryotic or eukaryotic metabolism, a mixture of component(s) derived from exogenous transformation including xenobiotic metabolism, a mixture of component(s) derived from genetically modified organism a mixture of component(s) derived upon activation with oxidative stress inducers, a mixture of component(s) derived upon chemical activation, a mixture of component(s) derived upon oxidation with peroxynitrite, a mixture of component(s) derived upon incubation with AAPH, a mixture of component(s) derived upon incubation with organic or inorganic peroxide, a mixture of component(s) derived upon air oxidation/aging, a mixture of component(s) derived upon auto-oxidation, a mixture of component(s) derived upon air oxidation, and/or UV exposure and/or thermal degradation.

Non-limiting examples of the electrophile includes reactive intermediates such as a $\alpha,\beta$-unsaturated carbonyl compound, an aromatic compound, an aliphatic compound, a terpene, sesquiterpene lactone, an epoxide, a polyphenol, a quinone, a polyhalogenated compound, a freshly prepared essential oil, an aged essential oil, essential oil aged under accelerated conditions, photo induced aged oil, or UV induced aged essential oil or enzymatically transformed essential oil, a crude plant extract or a fraction of plant extract obtained by various solvent, a commercial formulation including a fragrance, a perfume, a skin care product, a hair care formulation, an aromatherapy product.

In some embodiments, the presently disclosed subject matter discloses two complementary in chemico (non-biological, non-animal) methods for identifying and classifying chemical compounds as potential skin sensizitizers, using either NMR spectroscopic or microplate spectrophotometric methods. Further, in some embodiments, the presently disclosed subject matter provides a method for identification, classification and mechanistic studies of prehaptens. The method includes the combination of the steps of NMR method and/or microplate spectrophotometric assay and/or other spectroscopic methods. Still further, provided in some embodiments, is a method for identification classification and mechanistic studies of prohaptens. The method includes the combination of the steps of NMR method and microplate spectrophotometric method. Last, in some embodiments, the presently disclosed subject matter provides a method for identification classification and structure activity relationships of potential skin sensitizers including pre-pro-haptens. The method includes the combination of the steps of NMR method and microplate spectrophotometric method.

In some embodiments, the NMR method includes a process of mixing a nucleophile with a potential hapten (chemical) in an NMR tube, acquiring multiple spectra over a time period with predefined parameters and conducting a data elaboration process for evaluating and categorizating the potential hapten/sensitizer based on the variation of peak areas during the formation of conjugate adducts.

In some embodiments, this NMR method provides detailed structural information, including the amount of adduct formation. The reaction can be followed in time, thus providing kinetic information. The reactive site of the sensitizer candidate could be determined where multiple reactive sites may be present, when the reaction mechanism is unclear, or multiple reaction mechanisms could occur under the same reaction conditions. Thus, the proposed NMR technique is an information-rich method.

In some embodiments, the presently disclosed subject matter further relates to a method based on microplate spectrophotometry, including the following steps: mixing a fluorescent, luminescent, colored or UV-absorbing nucleophile with a chemical, such as a skin sensitizer; removing the unreacted nucleophile from the test substance in order to eliminate interference; quantifying the resulting conjugate using a multidetection microplate reader.

In some embodiments, this microplate spectrophotometric method serves as a potential method for the screening of complex mixtures, such as plant extracts, essential oils, perfumes as well as various unknown chemical allergens pure or in mixtures. In contrast to the NMR method, the potency of the allergen is determined by stopping the reaction after a fixed time frame and quantifying the product formation by spectrophotometric techniques. The microplate spectrophotometric method is extremely sensitive, it is fast, and multiple samples can be analyzed in a very short time frame. Thus, the techniques provided in the present disclosure would be especially valuable for screening of possible skin sensitization of unknown chemicals/candidates. These NMR and microplate spectrophotometric methods provided herein can be used alone or in combination for the identification of potential skin sensitizers in pure preparations, in complex natural extracts and/or in commercial formulations.

Both methods can be also combined with appropriate known or novel methods to identify and classify sensitizers including pre- or pro-haptens.

The presently-disclosed subject matter is further illustrated by the following specific but non-limiting examples. The following examples may include compilations of data that are representative of data gathered at various times during the course of development and experimentation related to the present disclosure.

EXAMPLES

The relevance of the disclosed spectroscopic approach is here exemplified by disclosing non-limiting examples of a NMR and a spectrophotometric method to identify and categorize potential skin sensitizers. The fluorescent compound, Dansyl CYsteAmine (DCYA) is here disclosed as non-limiting example of model nucleophile compatible with both the NMR and the microplate spectrophotometric method. Experimental values and parameters, concentrations, Stoichiometries, reaction times are also disclosed as non-limiting examples and each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Synthesis of Model Fluorescent Nucleophilic Thiol, Dansyl Cystamine:

N,N'-(disulfanediylbis(ethane-2,1-diyl))bis(5-(dimethylamino)naphthalene-1-sulfonamide) (DCYA disulfide)

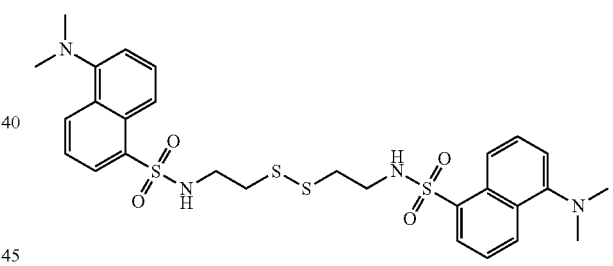

In a 250 mL round bottom flask, dansyl chloride (876.0 mg, 3.25 mmol) was dissolved in a solution of 90 mL of acetone and 3 mL of water. A solution of cystamine dihydrochloride (364.4 mg, 1.62 mmol, 0.5 equiv.) in 21 mL 0.1 M aqueous $NaHCO_3$ was added in portions. The solution was maintained to pH 7.5 by addition of aqueous 0.5 M sodium hydroxide. After 90 min at room temperature, the reaction mixture was diluted with 100 mL chloroform, and the solution was washed four times with aqueous sodium bicarbonate, followed by water. The organic layer was dried over anhydrous $MgSO_4$, concentrated and purified by column chromatography to 527.7 mg of dimer as a fluffy, crisp yellow solid (0.85 mmol, 53%), TLC $R_f$=0.25, 30% acetone in hexanes, mp 71-72° C.

$^1$H-NMR: (500 MHz, $CDCl_3$) δ 8.54 (d, J=8.5 Hz, 1H), 8.27-8.20 (m, 2H), 7.53 (ddd, J=15.9, 8.6, 7.4 Hz, 2H), 7.17 (d, J=7.6 Hz, 1H), 5.24 (t, J=6.2 Hz, 1H), 3.09 (q, J=6.3 Hz, 2H), 2.88 (s, 6H), 2.48 (t, J=6.3 Hz, 2H). $^{13}$C-NMR: (126 MHz, $CDCl_3$) δ 152.2, 134.5, 130.8, 130.0, 129.8, 129.6, 128.7, 123.3, 118.7, 115.4, 45.6, 41.7, 37.9.

5-(dimethylamino)-N-(2-mercaptoethyl)naphthalene-1-sulfonamide (DCYA)

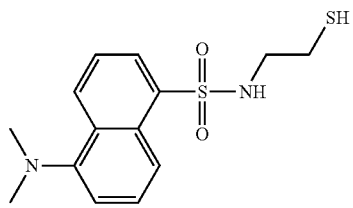 [SMILES: CN(C)c1cccc2c(S(=O)(=O)NCCS)cccc12]

In a 50 mL round bottom flask, the disulfide compound (0.324 g, 0.524 mmol) was dissolved in THF (18 mL) and water (2 mL), cooled to 0° C. and sodium borohydride (0.20 g, 5.29 mmol) was added in small portions. After 4 h, the solvent was evaporated and the residual was diluted with water and extracted with diethyl ether (3×10 mL). The combined organic layers were dried over anhydrous $MgSO_4$, concentrated and purified using a Biotage system to yield DCYA thiol as greenish-yellow fluffy solid. (TLC 30% EA in hexane, $R_f$=0.40)).

$^1$H NMR (500 MHz, $CDCl_3$) δ 8.56 (d, J=8.5 Hz, 1H), 8.28 (d, J=8.6 Hz, 1H), 8.25 (dd. J=7.3, 1.1 Hz, 1H), 7.61-7.56 (m, 1H), 7.53 (dd, J=8.4, 7.4 Hz, 1H), 7.20 (d, J=7.5 Hz, 1H), 5.18 (t, J=6.3 Hz, 1H), 3.08 (q, J=6.4 Hz 2H), 2.89 (s, 6H), 2.51 (dt, J=8.7, 6.3 Hz, 2H), 1.21 (t, J=8.7 Hz, 1H). $^{13}$C NMR (126 MHz, $CDCl_3$), 152.1, 150.1, 134.6, 130.7, 129.9, 129.6, 129.5, 128.6, 123.2, 118.5, 115.3, 45.9, 45.4, 24.8

Example 1: NMR Spectroscopy for Probing the Reactivity and Classification of Potential Skin Sensitizers A NMR spectroscopic method is described herein as non-limiting example of the potential application of the disclosed spectroscopic methods for the detection of potential sensitizers. The disclosed method takes advantage of unambiguous Nuclear Magnetic Resonance spectroscopy to accurately estimate the reactivity and classification of potential sensitizer by depending on depletion of electrophile signal rather than the conventional depletion of nucleophile. The described technique enables the direct quantification of hapten adducts and provides structural information including mechanistic domain. Dansyl cysteamine is here used as non-limiting example of fluorescent nucleophile. The described example can be applied to pure chemicals and mixtures. The method includes the acquisition of at least one NMR spectrum, mixing an electrophile and a nucleophile to acquire an array of control spectra and an addition of catalyst to record an array of reaction spectra. It also includes the quantification of at least one signal and the comparison of the signal with a control and the classification of the reaction based on the depletion of potential sensitizer based on the quantified residual signal.

Materials and Methods

Chemicals.

Cinnamaldehyde, p-benzoquinone, p-hydroquinone, 3-hydroxytyrosol, coumarin, curcumin, ethyl acrylate, citral, safranal, parthenolide, costunolide, alantolactone, 1,5-diazabicyclo[4.3.0]non-5-ene (DBN) and 2,5-dimethylfuran were purchased from Sigma Chemical Co. (St. Louis, Mo., USA). Massoialactone, trans-2-pentenal, (−)-carvone, (−)-perillaldehyde, nootkatone were kindly donated by Citrus and Allied Essences Ltd. (Lake Success, N.Y., USA). All deuterated solvents, chloroform-d, acetonitrile-$d_3$, and dimethylsulfoxide-$d_6$ were purchased from Cambridge Isotope Laboratories (Tewksbury, Mass., USA). Dansyl cysteamine (DCYA) was synthesized by following the modified reported procedure using commercially available dansyl chloride and cystamine hydrochloride.

NMR Spectroscopy.

Reactions were followed by mono-dimensional $^1$H NMR on an Agilent 500 MHz spectrometer (number of scans=4; gain=30; spectral size=74850, δ−1 to 14 ppm; acquisition time=5 sec; spectral width=7485.0 Hz; FID resolution=0.20 Hz; acquisition size=19461; delay time=20 s; Pulse width=30°, temperature=25° C.). Chemical shifts (δ) are reported in ppm relative to the $^1$H residual signal of the solvent peak ($CDCl_3$ 7.26, DMSO-$d_6$ 2.50 and acetonitrile-$d_3$ 1.94). 2,5-Dimethylfuran was used as internal standard. When necessary, characterization of the product(s) formed during the reaction(s) was performed by homonuclear $^1$H connectivities using 2D-COSY experiments. One-bond heteronuclear $^1$H-$^{13}$C connectivities were determined using gradient-HMQC experiments in which the interpulse evolution period was optimized to 3.45 µs. Two- and three bond $^1$H-$^{13}$C connectivities were determined by gradient-HMBC experiments in which the evolution period for long-range $^1$H-$^{13}$C coupling constants was optimized for a $^{2,3}J_{C,H}$ of 8 Hz. Through-space $^1$H connectivities were determined using a NOESY experiment with a mixing time of 0.450 s. Chemical shifts were compared with those calculated using ACD/C+H NMR Predictors and DB software [Release 2012, (Build 60488, 8 Nov. 2012), ACD/Labs. Toronto, Canada].

NMR Experimental Procedure.

In a 3 mm NMR tube, 1 volume of DCYA (100) mM in $CDCl_3$) was mixed with one volume of sensitizer (100 mM in $CDCl_3$) to give a final concentration of 50 mM for both DCYA and the sensitizer. Control $^1$H NMR spectra (reference spectra) were recorded at regular intervals of for a minimum of 5 min. After acquisition of control spectra, a catalytic amount of the catalyst was added (0.1 volume of 100 mM DBN in $CDCl_3$, 0.1 equiv.), and a series of spectra were recorded at regular intervals for a minimum of 5 min. All spectra were recorded at constant temperature. All experiments were conducted using the manufacturer's standard presaturation pulse programs and experimental conditions were chosen as explained in NMR spectroscopy section. The progress of the reaction was followed by the diminished peak areas of the resonances for the signal of interest. The spectra were phased, referenced, and integrated using NMR data elaboration software. The structural characterizations of the resulting adducts were confirmed by conducting additional 2D-NMR experiments when necessary.

Method Optimization

Figure 2:
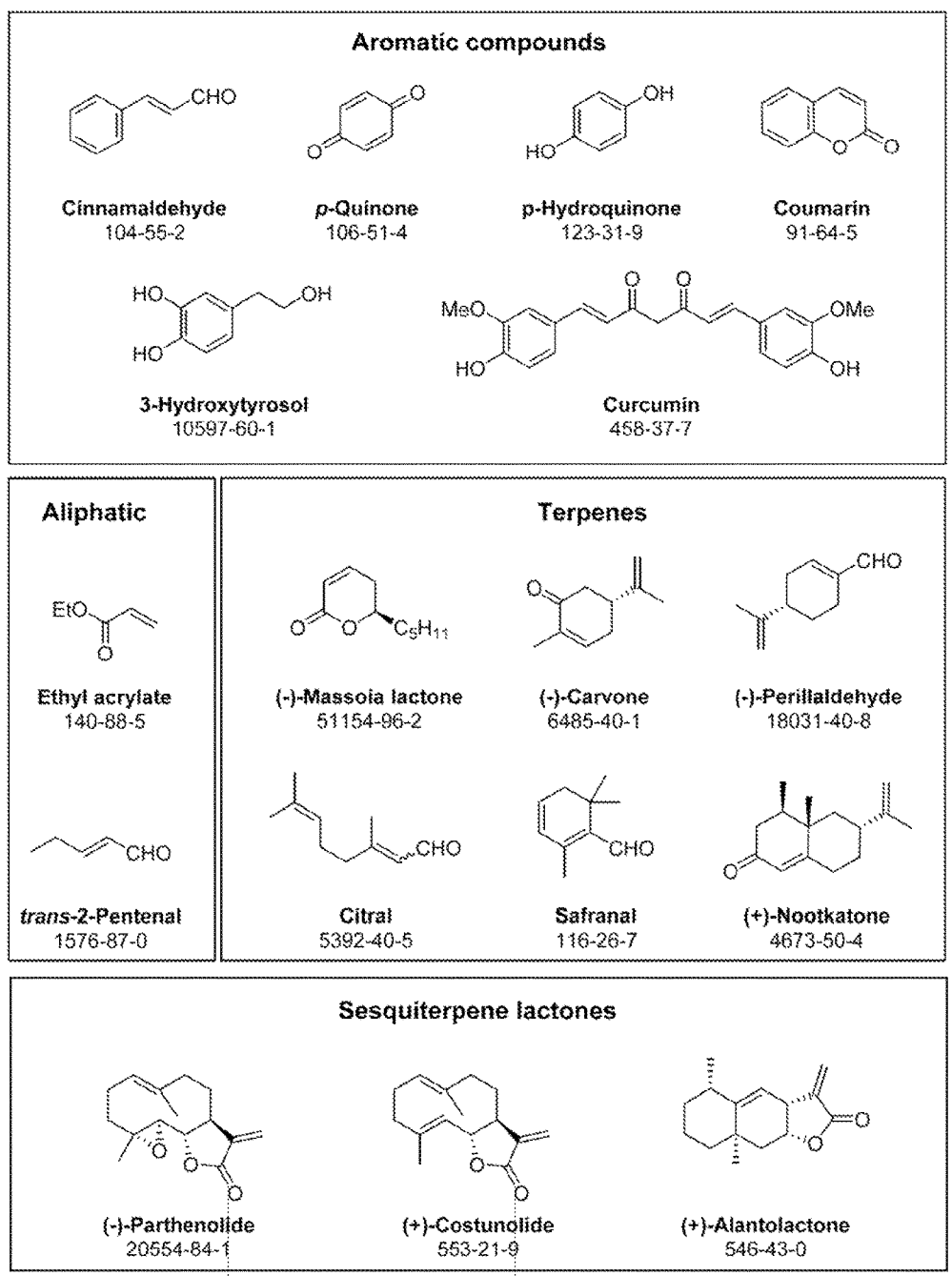
FIG. 2 shows the some of the select chemicals tested in NMR and high-throughput spectrophotometric methods.

In order to complement existing methods and overcome their existing limitations, an NMR spectroscopy method was developed to accurately estimate the reactivity and thus the categorization of the electrophilic haptens, it is necessary to measure the "real" adduct, and then classify the results based on the conversion. The structures of the tested potential sensitizers are shown in FIG. 2.

The weak/moderate sensitizer L-carvone was used as a model electrophile to determine the optimum reaction parameters for NMR investigations using a model nucleophile (DCYA). Covalent reaction of DCYA with carvone is dependent on the activation of the nucleophilic group (ex. sulfhydryl group to the reactive thio-anion) under basic conditions. This reaction is strongly dependent on the nature of the nucleophile and may be modulated by careful choice of the model nucleophile and the reaction conditions. For example, using the aliphatic nucleophile DCYA, the reaction was found to be controlled by pH variation upon addition of the basic catalyst 1,5-diazabicyclo[4.3.0]non-5-ene (DBN).

Scheme 1.

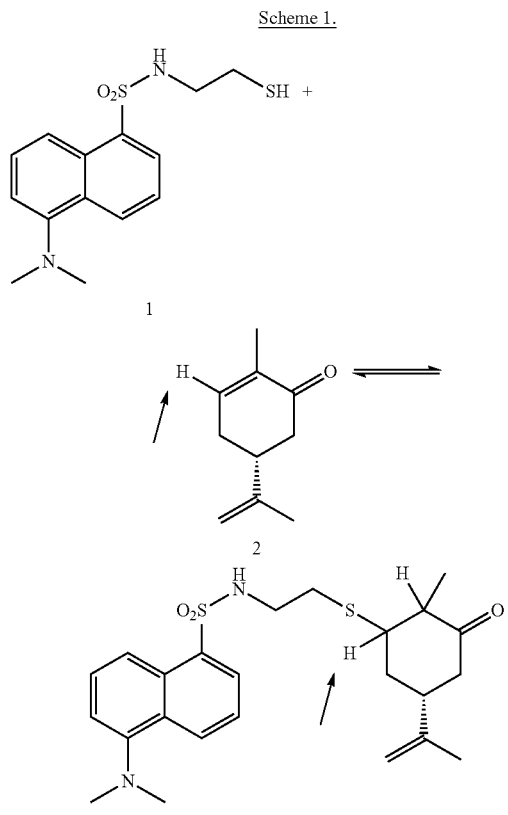

Example of reaction between DCYA (nucleophile) and L-carvone (electrophile) upon addition of a catalyst (DBN). The protons (indciated by arrows) corresponds to the signals monitored by NMR.

Figure 3A:
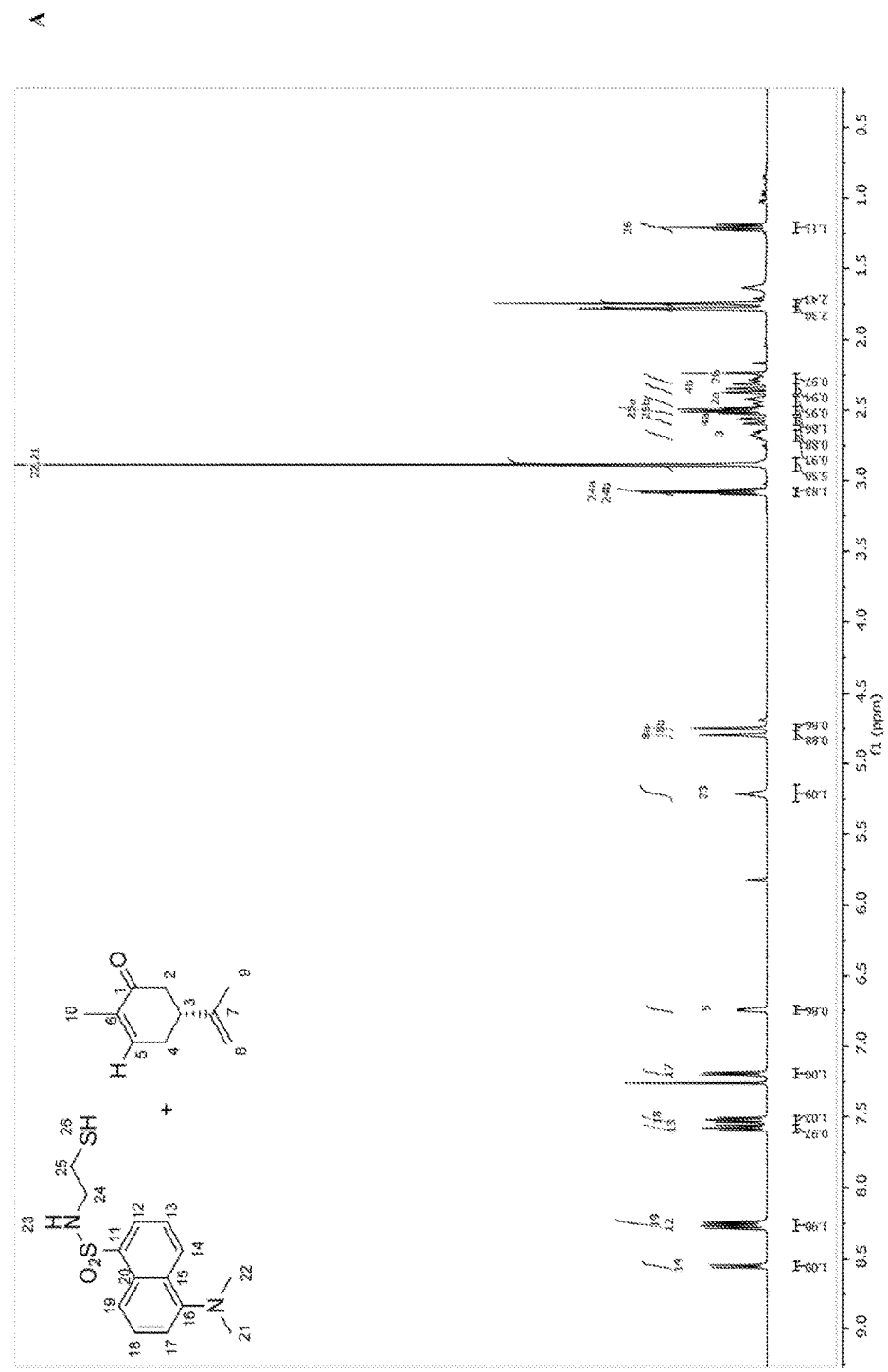
FIG. 3 shows: A) $^1$H NMR spectra of 1:1 mixture of DCYA and L-carvone before addition of DBN; B) an array of 7 $^1$H NMR spectra (500 MHz) of both DCYA and carvone collected for 9) min prior to the addition of a catalytic amount of DBN in CDCl$_3$; and C) an array of 11 $^1$H NMR spectra collected after the addition of DBN on a 300 minute period.
Figure 3B:
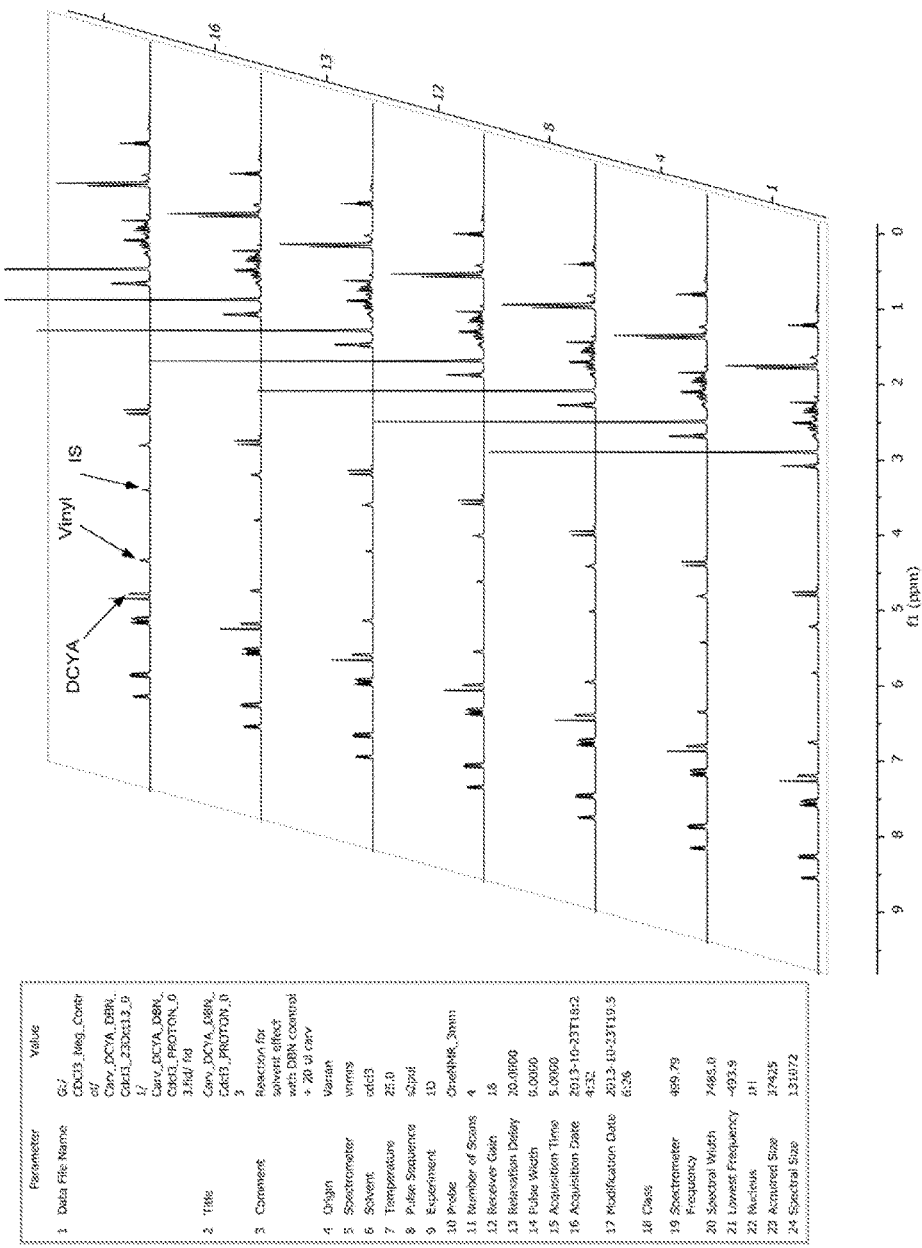
Figure 3C:
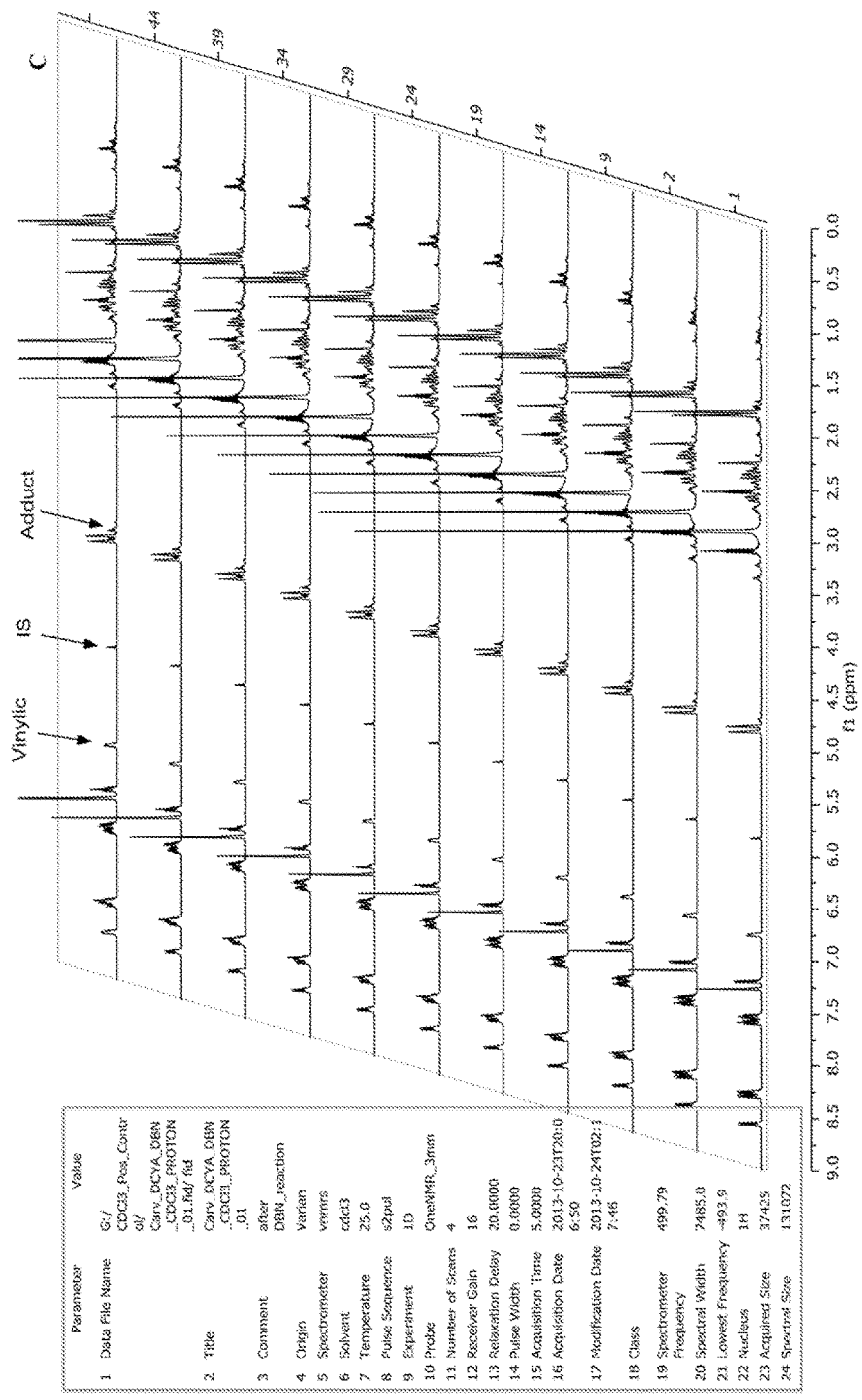
Figure 4:
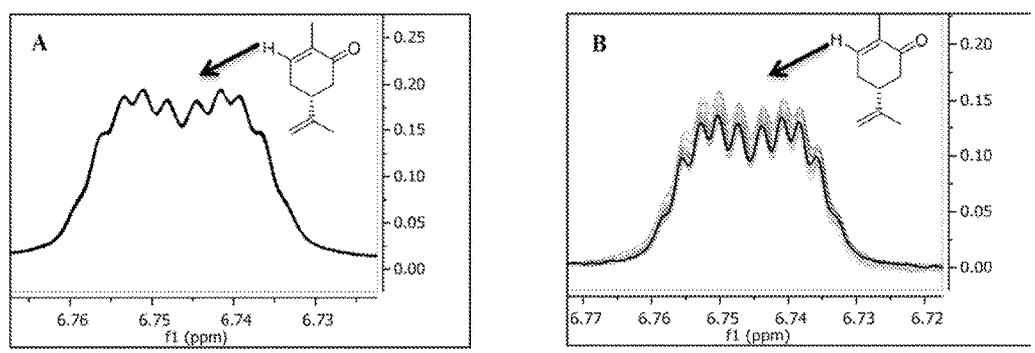
FIG. 4 shows the expansion of the arrayed spectra of FIG. 3 between $\delta$ 6.80-6.70 ppm, before (A) and after (B) the addition of DBN. After catalyst addition, the observed decrease of the area corresponding to the olefinic proton is related to the conversion of carvone in the reaction.
Figure 5:
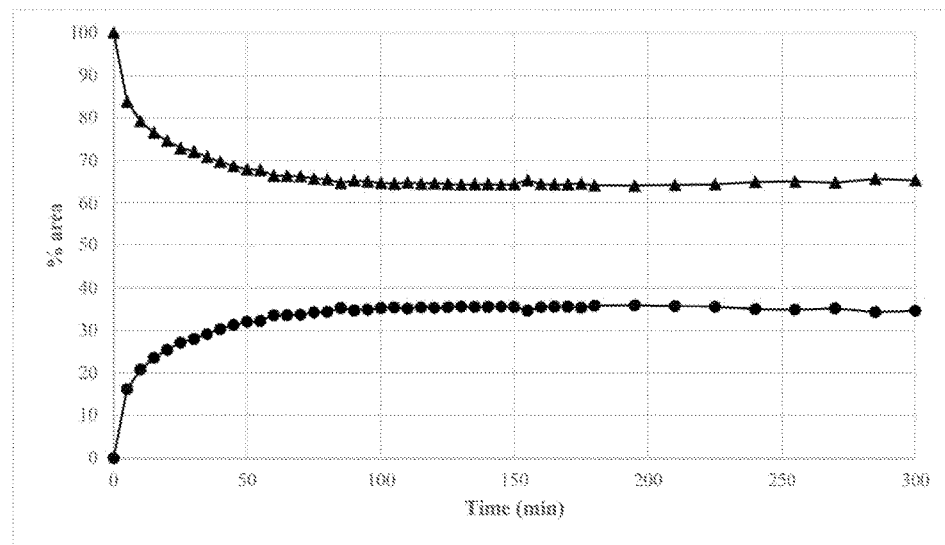
FIG. 5 shows the percentage of electrophile depletion and formation of adduct peaks for L-carvone and DCYA in a 300 minute time frame.

Two arrays were collected, one as a control and a second after addition of DBN (FIG. 3). The control spectra are used as reference spectra (FIG. 3A). All the spectra were subjected to automatic phase and baseline correction using a Bernstein polynomial fit (order 3). After these two steps, all the spectra were integrated over the areas of interest. For example, in the experiments with carvone, the integral values for carvone were collected for vinylic proton between δ 6.80-6.68, the internal standard (dimethyl furan) between δ 5.85-5.78 and adduct peak between δ 4.72-4.66. Both vinylic and adduct peak areas were normalized relative to the internal standard signal peaks. As shown in FIG. 3B, the concentration of carvone remained constant until addition of DBN as a catalyst. Upon addition of the catalyst, the reaction was monitored in a 90 minutes frame showing a progressive decrease in carvone concentration with time (FIGS. 3C and 4). This system reached the equilibrium in less than 100 minutes and did not change in the 5 hour time frame. The concentrations of both electrophile and adduct were then plotted as percentage against time (in minutes). (FIG. 5).

In order to determine which experimental parameters were crucial for the success, validity and viability of the proposed technique, the effect of several different parameters e.g. thiol type, catalyst, solvent, temperature and stoichiometry was explored utilizing the model reaction. The results of these studies are summarized in FIG. 6.

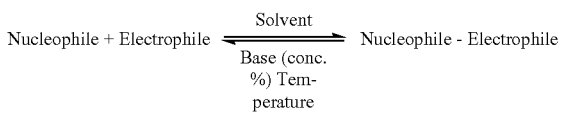

Type of Thiol.

Figures 6A, 6B, 6C, 6D, 6E, 6F:
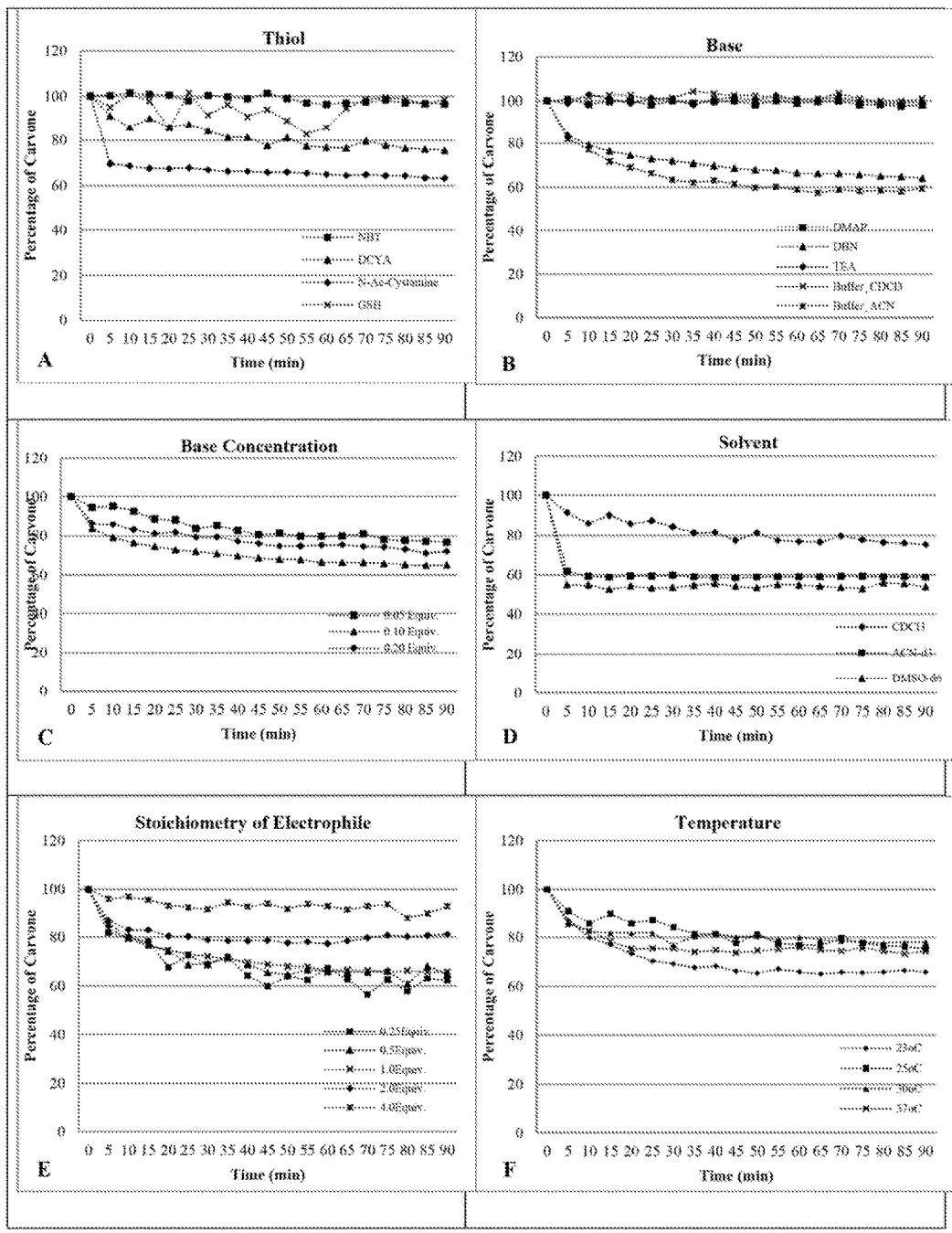
FIG. 6 shows the role of different parameters on the outcome of the adduct formation between nucleophile and electrophile, carvone. The percentages were calculated from the peak intensity of the vinylic proton of the carvone (depletion of peak at $\delta$6.8 with respect to internal standard, dimethyl furan's peak at $\delta$5.9 ppm). All results are expressed as a percentage of nucleophile remaining.

Different thiols that have been used as model nucleophiles for skin sensitization assays were tested in DMSO-$d_6$. The choice of the solvent for the investigation of the thiol effect is affected by the poor solubility of some of the selected thiols in many solvents. Various thiol candidates were tested in these methods and some of the examples are mentioned here given in parenthesis. Aromatic thiols were used, such as 4-nitrobenzenethiol (NBT), peptides (glutathione. GSH) and aliphatic thiols (N-acetyl cysteamine, NAC and dansyl cysteamine, DCYA) (FIG. 6A). The solubility of the nucleophile may influence the chosen reaction condition that can be used in order to take into account different lipophilic properties of potential sensitizers, which are known to have log $P_{oct/wat}$ greater than 1.[27] The use of a two-solvent system has been previously suggested[13, 15, 48] to by-pass solubility issues, but these conditions are not ideal in estimating the reaction kinetics and classification of potential skin sensitizers.

The aromatic thiol NBT gave a slow reaction with a poor conversion rate (<4% in 90 minutes). Aromatic thiols are known to be less reactive than aliphatic ones, and even if some of them (such as NBT) are considered as a surrogate for protein thiols,[49] the long reaction times in the chosen conditions represent a major drawback in NMR spectroscopic method.

Reaction with aliphatic thiols gave better reaction kinetics, with initial 30% conversion, which is eventually stabilized to around 33% after 5 h. The conversion rates are comparable along examples of thiols in the same reactivity class (FIG. 6A). Both NAC and DCYA show a similar reactivity profile, which confirmed the similarity between the designed fluorescent thiol and the nonfluorescent model nucleophile, NAC. Thus, the designed fluorescent thiols (represented here by the example of DCYA) and biologically significant non-fluorescent thiols presented a similar reactivity profile. Based on these observations, the designed fluorescent thiols possess a biologically significant reactivity feature combined with adaptability to high-throughput screening purposes.

The Effect of Basicity.

Because the reaction of the nucleophile with carvone is dependent on the activation of the nucleophile by a catalyst, the reaction rate of carvone with DCYA upon addition of different basic catalysts was explored in $CDCl_3$. As an example, different organic bases possessing different pKa values and an aqueous inorganic buffer were chosen for investigation. The basicity effect was evaluated using a catalytic amount (0.1 equiv. for each equiv. of DCYA). The results shown in FIG. 6B indicate that the tertiary amine triethylamine (TEA, pKa 10.8) and the aromatic amine dimethylamino pyridine (DMAP, pKa 9.2) did not show any catalytic effect. The aqueous pH 10 buffer (5% v/v) was sufficient to catalyze the reaction between DCYA and carvone in acetonitrile in less than 5 minutes, with a reaction of 42% after 90 minutes. The nature and basicity of the catalyst affect the kinetics of the reaction. The kinetic effect of a base is also strongly affected by the solvent used in the reaction. The base effect on thiol addition is well known where the equilibrium Base+RSH ⇌ BaseH$^+$RS$^-$ is dominant. It has been estimated for example that the use of DBU rather than TEA in CH$_2$Cl$_2$ and DMSO can provide >4 kcal/mol of driving force.[50] The results here presented are in agreement with the reported observations, confirming the significant role of bases on the equilibrium enone/thioether. The combination of solvent/catalyst has therefore to be adjusted in order to avoid the possible interference of a two-solvent system in the kinetic experiments with NMR.

The Effect of Catalyst Concentration.

The effect of DBN concentration was evaluated on the model reaction L-carvone/DCYA in chloroform (FIG. 6C). Variation of DBN concentration 0.05, 0.1 and 0.2 equivalents with respect to 1.0 equivalent of DCYA showed depletion of 23, 35 and 28% respectively, with 0.1 equiv. DBN being the best condition in terms of reaction conversion and time. The optimum conditions were then chosen as 0.1 equiv. of catalyst for each 1 equivalent of nucleophile, DCYA.

Solvent Effect.

The effect of the type of solvent was investigated using 0.1 equiv. DBN, 0.1 M DCYA and 0.1 M L-carvone in various solvents. The results for polar, aprotic solvents acetonitrile and DMSO, as well as the non-polar solvent chloroform are shown (FIG. 6D). The solvent choice is strongly related to the choice of the nucleophile and compatible with the solubility properties of the electrophiles to be tested. Two-solvent systems were avoided in kinetic experiments. Polar aprotic solvents performed best in terms of reaction conversion (47 and 42% of conversion rate, respectively). Because of the high solvent—effect on the model reaction, caution should be used if comparing electrophilic reactivity in different solvents. The effect of DMSO on disulfide formation has been previously observed by Böhme et al. for glutathione, thus the pro-oxidization effect of the solvent should be taken into account when DMSO is used.[51]

Stoichiometry.

The influence of the electrophile on the reaction was observed. The experimental data reported for L-carvone and DCYA in chloroform using 0.1 M thiol and 0.1 equiv. DBN. Stoichiometries from carvone: DCYA 1:4 to 4:1 were investigated (FIG. 6E). In the presence of an excess of DCYA, the reaction stabilized around 37% of electrophile depletion. The results show that there was no significant effect on the reaction rate with an excess of DCYA. On the other hand, increasing the excess of electrophile negatively affected the reaction rate, which decreases to 21 and 8% of depletion for 2 equiv. and 4 equiv. of DCYA, respectively.

Temperature Effect.

Variation in the temperature from 23 to 37° C. affected the reaction in a range <12% (FIG. 6F). Based on these results, experiments performed at room temperature were preferred and are likely to be representative of in vivo temperature as well.

Discussion

To mimic skin chemistry, the majority of the state-of-the-art in chemico methods are based on the depletion of the nucleophile of interest. However, these approaches are known for over- or under-estimation of potential skin sensitizers due to unwanted side products such as drowning-out effects, autoxidation of thiol nucleophiles.[18, 24, 40] To overcome such difficulties, herein a method based on reactivity and classification of potential sensitizer by depending on "depletion of electrophile signal (doEs)" rather than the conventional "depletion of nucleophile". The proposed method takes advantage of unambiguous Nuclear Magnetic Resonance spectroscopy. Additionally, NMR spectroscopy could serve as an ideal tool for accurately estimating the reactivity of electrophilic (sensitizer) candidates, the rate of reaction and the quantification of NMR signal of interest. A series of structurally diverse, naturally occurring electrophiles were divided in four main categories according to their structural features. The structures of the compounds are shown in FIG. 2. All the listed potential skin sensitizers were investigated for their depletion potential using the optimized NMR conditions. The compounds have been grouped according to their chemical structure, and the depletion results are shown in FIG. 7.

Aromatic Compounds

Compounds containing α,β-unsaturated ketones in extended conjugation with an aromatic moiety were herein classified as aromatic compounds. This definition embraces a number of different structurally diverse compounds. The type and position of the extended conjugation may play an important role in determining the electrophilic behavior of the candidate compounds. Many of these compounds, like cinnamaldehyde,[52] could be formally classified under a different mechanistic domain and such ambiguity may be an important limitation when using indirect assays or in silico screening.[53] Some of these compounds, like p-benzoquinone and cinnamaldehyde, are also known for their oxidizing properties.[15] Traditional methods based on LC-MS or indirect peptide depletion assay do not give any mechanistic information on the reactivity of these compounds, where identifying and classifying the type of reactivity could actually be crucial for risk assessment concerning skin sensitization. The proposed NMR method may provide very useful insights on the kinetics and mechanisms of reaction, which could be also used for improving in silico hazard assessment methods. Cinnamaldehyde is classified as a moderate sensitizer and used as a positive control in KeratinoSens™ assays.[52] In the proposed NMR assay, cinnamaldehyde was also identified as a moderate sensitizer, with 50% depletion after 30 minutes. Whereas, benzoquinone, known strong sensitizer,[54] showed a high reactivity with >95% depletion in less than five minutes (FIG. 7A).

A moderate reaction was also determined by NMR for the phenolic natural product curcumin. Curcumin's electrophilic behavior is complicated and unpredictable with in silico screenings. The bis-keto enone moiety can be formally classified as a double Michal acceptor site, which would make this molecule a potentially strong sensitizer. On the other hand, the structure of curcumin is known to exist in a keto-enolic equilibrium rather than as a diketone.[55] The resonance effect could have a negative impact on the electrophilicity of the unsaturated double bond by interfering with its conjugation. Moreover, both Michael acceptor sites are highly conjugated, on one side to the aromatic ring, on the other site to the second α,β-unsaturated keto residue. Curcumin is also known for its antioxidant properties, where the central methylene donor could act as a hydrogen donor through radical mechanisms.[56] Altogether, these features make curcumin a complex, unpredictable skin sensitizer, where in silico methods could actually fail in quantification and classification. The reaction with curcumin was performed in DMSO-d$_6$ due to the low solubility of this electrophile in chloroform. From the NMR results presented in Table 1, curcumin was classified as moderate reaction, with 43% depletion using a double amount of nucleophile (the amount of nucleophile must be proportioned to the number of potentially reactive sites). Dimethyl sulfoxide has a strong solvent effect on the dynamic of the reaction (FIG. 6D). Translating the reactivity to chloroform (which is the solvent through the text as example), where reactivity drops more than 20% in the same conditions (FIG. 6D), the predicted reactivity of curcumin in chloroform would be lower than the calculated one (FIG. 7A). This result was somewhat unexpected considering that curcumin possesses multiple reactive site, but also explains the low incidence of skin sensitization reported for curcumin, considering the large use as colored agent as well as for topical usage in traditional Eastern medicine.[57]

Figures 7A, 7B:
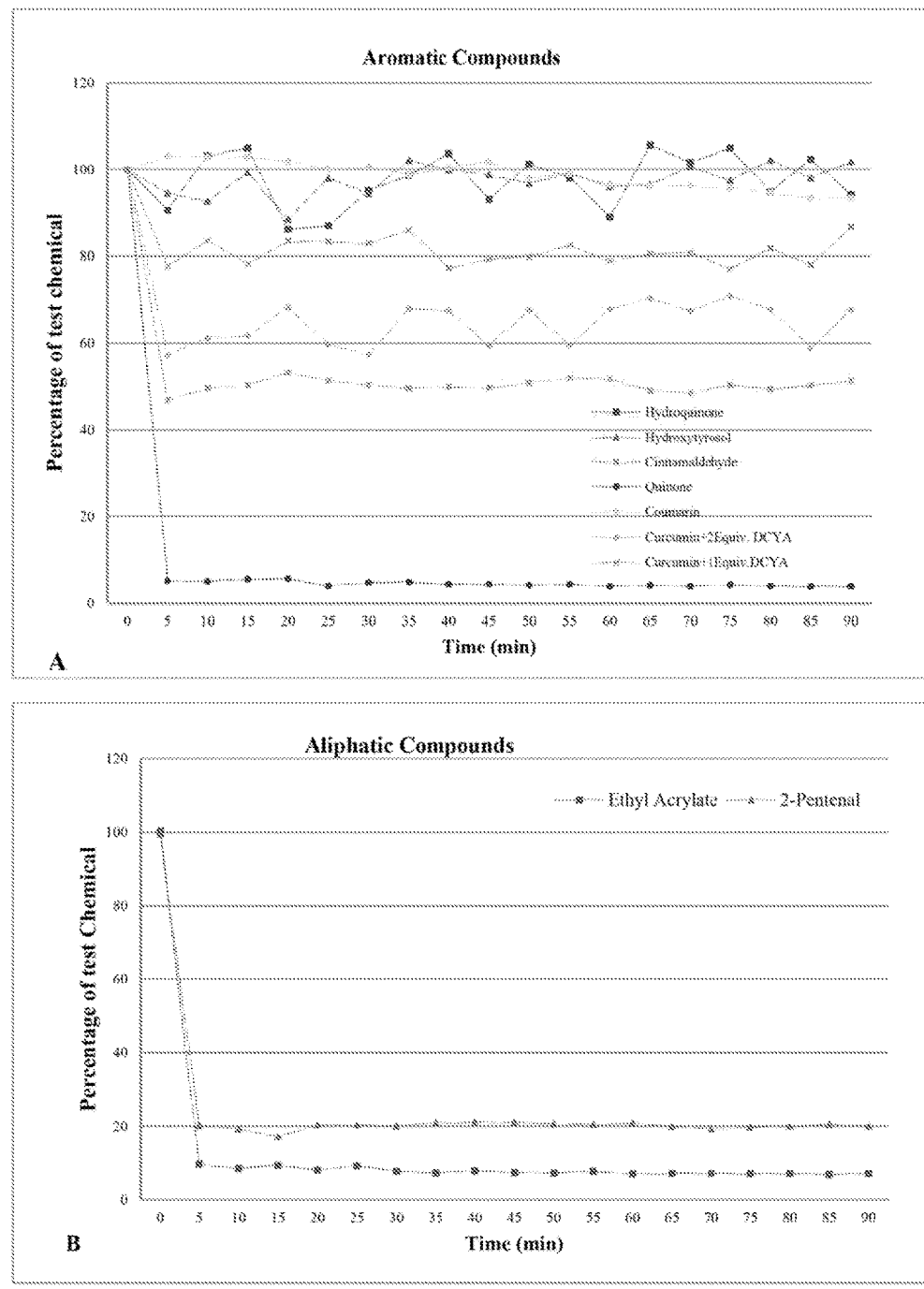
FIG. 7 shows the experimental results for the NMR method for different classes of potential sensitizers. Values are expressed as relative area of the vinylic or aromatic proton (for nonvinylic) $^1$H plotted against time. Aromatic compounds (A), aliphatic compounds (B), terpenes (C) and sesquiterpene lactones (D) are tested.

Coumarin, hydroquinone and hydroxytyrosol were almost unreactive (FIG. 7A). Coumarin is a known photosensitizer and has been earlier classified as skin sensitizer, but Vocanson et al.[58] demonstrated that this natural benzopyrone is not responsible for skin sensitization, thus these results corroborated the biological evidence. Hydroxytyrosol and hydroquinone do not possess classical mechanistic domains that explain their categorization as strong sensitizers from LLNA data. It is suggested that both compounds actually require some kind of activation to the reactive hapten. In other words, they may be classified as pre- or pro-haptens.[25]

Aliphatic Compounds

One $\alpha,\beta$-unsaturated ester and one $\alpha,\beta$-unsaturated aldehyde were chosen for the study of aliphatic compounds reactivity. Ethyl acrylate is a volatile synthetic compound, which is known for its sensitization properties.[59] Ethyl acrylate resulted in false negative results from LLNA data, due to its high volatility and to the tendency of polymerizing upon air exposure.[60] Comparing the reactivity of ethyl acrylate with the aliphatic aldehyde t-2-pentenal, the NMR results ((FIG. 7B) confirmed the general finding of aldehydes less reactive than unsaturated esters.[61] Skin sensitization data were not available on t-2-pentenal, but its homolog t-2-hexenal has been classified as moderate sensitizer,[62] and Chan et al. found t-2-pentenal to be more reactive with thiols compared to t-2-hexenal.[63]

Terpenes

Figures 7C, 7D:
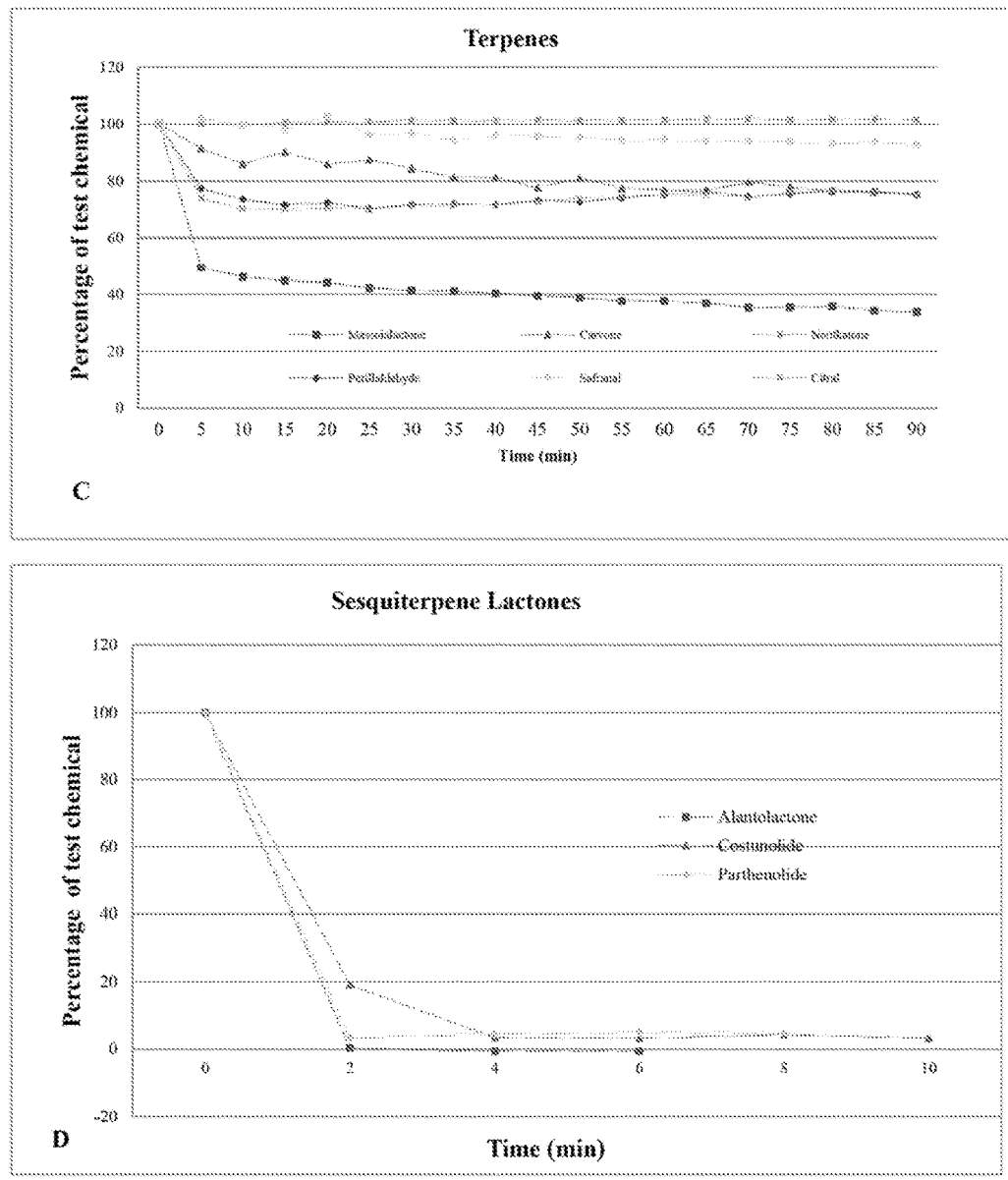

The majority of potential sensitizers from natural sources are volatile compounds belonging to the terpenoids class, and they can be found in essential oils and fragrances. Among the selected compounds, 60% of depletion was observed for massoia lactone within 30 minutes suggesting reactive nature of the perfume's constituent as moderate to strong skin sensitizer. On the other hand, the sesquiterpene nootkatone was found to be non-reactive, probably due to highly substituted electrophilic double bond and steric hindrance. The two aldehydes perillaldehyde and citral both showed a moderate/low electrophilic behavior, which is congruent with their LLNA data.[20, 62, 64] The moderate[60] sensitizer safranal was found to be less reactive by NMR in the short time frame, but more reactive if considered in a longer time frame (<3 h) (FIG. 7C).

Sesquiterpene Lactones:

Sesquiterpene lactones are probably the most common contact allergens isolated from plants,[65] especially from the Asteraceae family, one of the largest flowering plant families in the world. The sesquiterpene lactone mix (costunolide, dehydrocostuslactone, and alantolactone)[66] and the Compositae mix have been developed as screening tools for clinical patch tests.[67] Parthenolide and herbal extracts containing sesquiterpene lactones are known to cause severe allergic contact dermatitis.[68] Structurally, the epoxide and the $\alpha,\beta$-unsaturated lactone ring of parthenolide can compete as reactive sites for nucleophilic thiol addition. The majority of the reported methods relying on mass spectrometry would reveal only the presence of adduct and depletion of thiol without any structural information. When tested in the NMR method with one equivalent of DCYA, these sesquiterpene lactones instantaneously reacted (<5 min) (FIG. 7D) with irreversible disappearance of the exocyclic double bond signals. Moreover, NMR indicated the exclusive regioselective formation of parthenolide-DCYA adduct due to reaction at the exomethylene-$\gamma$-lactone site over the epoxide position. The specificity of the thiol attack was previously reported by using cysteamine as a nucleophilic trap for irreversible Michael acceptors.[69] Neither dimerization of the thiol to disulfide nor lactone thiolysis was observed in all tested sesquiterpene lactones, indicating the selectivity for Michael addition versus other reaction modes in substrates containing multiple electrophilic sites.

TABLE 1

Comparison of hapten depletion obtained by NMR method with published literature LLNA, Cys-DPRA and KeratinoSens™ data.

| Test Chemical | LLNA Classification (EC$_3$)[1] | NMR Method conversion[2] | Cys-DPRA[3] | KeratinoSens™ EC$_3$ [μM] | Reference and comments |
|---|---|---|---|---|---|
| 3-Hydroxytyrosol | Strong (0.6) | 6 | n.a. | n.a. | Pre/pro-hapten[70] |
| Coumarin | Non (NC) | 0 | 1 | 479.96 | Ref.[64] |
| p-Hydroquinone | Strong (0.11) | 5 | 83.3 | 51.29 | Pre/pro-hapten[64] |
| Safranal | Moderate (7.5) | 4 | 90.5[15] | n.a. | Ref.[60] |
| Nootkatone | n.a. | 0 | n.a. | n.a | |
| L-Carvone | Moderate (13 or 10.7) | 16 | 26.3[20] | 258.71[20] | Ref.[71] |
| Curcumin[4] | n.a. | 18 | n.a | n.a. | |
| Perillaldehyde | Moderate (8.1) | 28 | 31.9 | 61.85 | Ref.[64] |
| Citral | Moderate (9.2) | 29 | 85.7 | 67.36 | Ref.[64] |
| Curcumin[5] | n.a. | 43 | n.a. | n.a. | |
| Cinnamaldehyde | Moderate (3.0) | 50 | 70.6 | 63.94 | Ref.[64] |
| Massoia lactone | n.a | 66 | n.a. | n.a. | |
| t-2-Pentenal | n.a. | 80 | n.a | n.a. | |
| Ethyl acrylate | Weak (28.0) | 93 | 96.4 | 231.19 | Ref.[64] |

TABLE 1-continued

Comparison of hapten depletion obtained by NMR method with published literature LLNA, Cys-DPRA and KeratinoSens ™ data.

| Test Chemical | LLNA Classification (EC$_3$)[1] | NMR Method conversion[2] | Cys-DPRA[3] | KeratinoSens ™ EC$_3$ [µM] | Reference and comments |
|---|---|---|---|---|---|
| Parthenolide | n.a. | >95* | n.a | n.a. | Positive in human patch tests[6] |
| p-Benzoquinone | Extreme (0.01) | 95# | 99.0 | 32.77 | Ref.[64] |
| Costunolide | n.a. | >97* | n.a. | n.a. | Positive in human patch tests[6] |
| Alantolactone | n.a. | >99* | n.a. | n.a. | Positive in human patch tests[6] |

[1] Effective concentration is reported as percentage per microgram per cm$^2$;
[2] conversion percentage of test chemical at 90 min determined by NMR experiment;
[3] Percentage of thiol peptide depleted, adopted from the literature;
[4] One equivalent of DCYA was used;
[5] Two equivalents of DCYA was used;
[6] These sesquiterpene lactones are reported positive in human Patch tests[37]
*Due to their rapid reaction, spectra for these entries were collected for 10 min only;
5% of dimeric DCYA was also observed.
NC = Non classified;
n.a. = not available.

TABLE 2

NMR Classification of potential sensitizers based on depletion of electrophile signal at 30 min.

| | Test chemical | Conversion at t$_{30}$ | Classification |
|---|---|---|---|
| 1 | Hydroxytyrosol | 6 | Non$ |
| 2 | Coumarin | 0 | Non |
| 3 | Hydroquinone | 5 | Non$ |
| 4 | Safranal | 3 | Non |
| 5 | Nootkatone | 0 | Non |
| 6 | L-Carvone | 16 | Weak |
| 7a | Curcumin | 17# | Weak |
| 8 | Perillaldehyde | 28 | Weak-moderate |
| 9 | Citral | 29 | Weak-moderate |
| 7b | Curcumin | 43* | Moderate |
| 10 | Cinnamaldehyde | 50 | Moderate |
| 11 | Massoialactone | 59 | Moderate-strong |
| 12 | t-2-Pentenal | 80 | Strong |
| 13 | Ethyl acrylate | 92 | Strong |
| 14 | Parthenolide | 95 | Strong |
| 15 | p-Benzoquinone | 95 | Strong |
| 16 | Costunolide | 97 | Strong |
| 17 | Alantolactone | 99 | Strong |

Only one equivalent of DCYA was used.
*Two equivalents of DCYA was utilized.
$Pro-electrophile sensitizers are likely to be falsely predicted as non-sensitizers.

Overall, based on NMR method, all test chemicals were grouped based on conversion of electrophile's signal and categorized as non, weak, moderate, and strong entities. From the Table 2, the NMR-based classification appears reasonably reliable in delineating the categorization of potential sensitizers from non, weak, moderate, strong reactivity nature. In order to get a reliable reactivity index for potency estimation, the NMR methodology could very easily be adapted to do kinetics and estimate the rate constant for each test substance. Accessibility of such resulting rate constants may be useful on quantitative prediction of potency by quantum mechanics modeling (QMM) or read-across methods. Moreover, the developed NMR method should serve as a qualitative and quantitative tool in understanding the site of reaction and structural information associated with skin sensitizers. This is a particularly valuable and advantageous over the currently endorsed methods, which merely provide a quantification of the reaction but lack any structural information.

Figure 8:
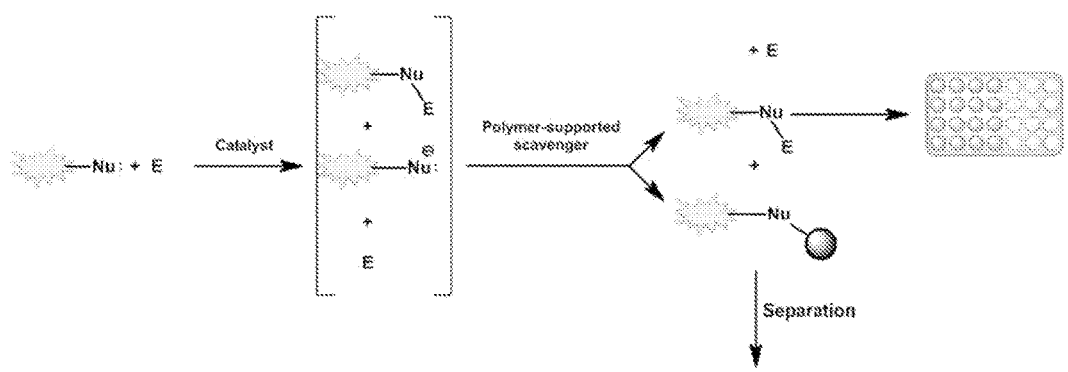
FIG. 8 shows the reaction overall scheme for the microplate spectrophotometric method.

Example 2: Microplate Spectrophotometric Method for Rapid Detection of Potential Skin Sensitizers A microplate spectrophotometric method is described herein as non-limiting example of the potential application of disclosed spectroscopic methods for the simultaneous detection of multiple potential skin sensitizers. The described technique enables the direct quantification of reaction adduct(s) between test article (sensitizer) with the model nucleophile in a fast, simple and sensitive manner. Furthermore, the described method can be applied to pure test chemicals or complex mixtures. The microplate method is designed to use a model nucleophile which can be attached to a fluorescent, luminescent or colored tag. Dansyl cysteamine is here used as non-limiting example of fluorescent nucleophile. The nucleophile is incubated for a short time period with the candidate electrophilic compound and a catalyst. Subsequently, the excess of unreacted nucleophile is removed by a polymer-supported scavenger in order to selectively quantify the fluorescence response of the reaction products. The nucleophile which has reacted with the electrophilic compound to yield an uncharged complex will not be retained on the scavenger, and thus can be recovered and used to calculate the degree of complex formation. The overall reaction scheme is shown in FIG. 8.

Materials and Methods

Chemicals and Reagents.

Diphenyl cyclopropenone, p-benzoquinone, 1-chloro-2,4-dinitrobenzene, p-hydroquinone, propionolactone, 3-hydroxytyrosol, 1,2-cyclohexanedicarboxylic anhydride, 2-methyl-4-isothiazolin-3-one, cinnamaldehyde, 2,4-heptadienal, 4-hex-3-en-one, squaric acid, trans-2-hexenal, resorcinol, diethyl maleate, lilial, cinnamyl alcohol, cis-6-nonenal, 5-methyl-2,3-hexanedione, ethyl acrylate, aniline, 1-bromobutane, vanillin, tartaric acid, chlorobenzene, lactic acid, salicylic acid, coumarin, benzaldehyde, citral, farnesal, safranal costunolide, alantolactone, parthenolide, oxalic acid, benzyl benzoate, standardized buffer solution pH 7 and 1,5-diazabicyclo[4.3.0]non-5-ene (DBN) were purchased from Sigma Chemical Co. (St. Louis, Mo., USA). Massoialactone, trans-2-pentenal, L-(−)-carvone, (−)-perillaldehyde and nootkatone were kindly donated by Citrus and Allied Essences Ltd. (Lake Success, N.Y., USA). Polymer-supported maleimide (SiliaBond® Maleimide, >0.64 mmol/g) was purchased from SiliCycle (Quebec City, Quebec, Canada). Microcentrifuge tubes and polypropylene solventresistant 96-well microplates, buffer solutions and TLC silica gel supported on aluminum sheets (without fluorescence indicator) were purchased from Fisher Scientific (Suwanee, Ga., USA). Certified potassium buffer solution pH 10 was purchased from Fischer Scientific (Pittsburgh, Pa., USA). Microcentrifuge 5415 C was purchased from Eppendorf (Hauppauge, N.Y., USA). TLC silica gel 60 supported on aluminum sheets (without fluorescence indicator) was purchased from EMD Chemicals (Darmstadt. Germany).

Spectrophotometry.

The microplate assays were performed on a SpectraMax M5 Multi-Mode Microplate Reader (Molecular Devices, Sunnyvale, Calif., USA). The spectrophotometric assays were performed using end-point, full spectrum or kinetic analysis. Data were acquired and processed using SoftMax Pro 5 (Molecular Devices, Sunnyvale, Calif., USA) or appropriate software. A calibration plot for the appropriate nucleophile used was performed before the test. The samples were evaluated using end point readings and full spectrum profiles for fluorescence and absorbance. Fluorescence end-point readings were acquired at 520 nm (excitation 350 nm), temperature 23° C. Full emission spectra were recorded over a range of emission wavelengths from 420 to 700 nm (excitation 350 nm). Absorbance profiles were recorded on a range 380-750 nm.

Experimental Procedure.

Spectrophotometric assays of potential sensitizers were performed using 96 well microplates. For the reaction, one volume of a 2.5 mM solution of DCYA was mixed with an equal volume of 5.0 mM solution of electrophile (2.0 equiv.). Aqueous pH 10 buffer (1:5 v/v) was added to the resulting solution and the mixture was incubated for 10-60 min while shaking at room temperature. For blanks, acetonitrile was added in place of the buffer. For positive and negative controls, one volume of acetonitrile was added in place of electrophile solution. All samples (Table 3; controls, blanks and reaction) were then treated in the same manner. The reaction was stopped by adding (10-200 mmol equiv.) of silica-supported maleimide. The samples were vortexed and incubated for 5-300 min with vigorous shaking at room temperature. The supernatant solution was then, diluted to a known volume with acetonitrile and the samples were transferred to microplate for spectrophotometric analysis.

TABLE 3

Details of the reagents for the sample preparation

|  | DCYA | Test article | Buffer | Resin |
|---|---|---|---|---|
| Reaction (R) | + | + | + | + |
| Blank (Bl) | + | + | − | + |
| Positive control (PC) | + | − | − | + |
| Negative control (NC) | + | − | + | + |

Thin Layer Chromatography (TLC).

For visualization purposes, the controls, blank and reactions were monitored by TLC on silica gel plates. A known volume of each sample was loaded on a silica gel plate and eluted with appropriate solvent system. The TLC plates were examined $\lambda_{366}$ for the presence of the yellow fluorescence spots corresponding DCYA, its dimer or possible reaction products.

Method Optimization.

The two proposed screening methods (NMR and microplate) are based on a similar rationale, but the classification for the skin sensitizer is determined using different approaches. The NMR method can provide insight on the mechanistic domain involved. Structural information can be achieved and the potency of the electrophile is classified based on the progressive electrophile depletion over the time. There is no need for separation of mixtures, as signals deriving from the reacted and unreacted species are unique and can be easily identified. The formation of byproduct (DCYA disulfide) was minimal under tested conditions.

The spectrophotometric method was intended to complement the NMR study by providing a quick tool for analyzing multiple samples with a minimum amount of test material. It is also optimal for screening of mixtures where the aim is to see whether the sample contains any potential sensitizers, even if they are present in very low concentration. In this fluorescence assay, for example, the degree of reaction is determined by analyzing and quantifying the amount of reacted nucleophile. Because of the very high sensitivity achievable using this method (over 100 times more sensitive than NMR), the reaction conditions must be optimized under highly diluted conditions to accomplish a significant discrimination across a range of reactivity from non-sensitizers to strong-sensitizers. Preliminary experiments were monitored by TLC to quickly determine the experimental parameters to be optimized. The same conditions were then translated into a suitable spectrophotometric method by using a microplate reader.

Excitation, Emission and Calibration of DCYA.

Figures 9A, 9B, 9C, 9D:
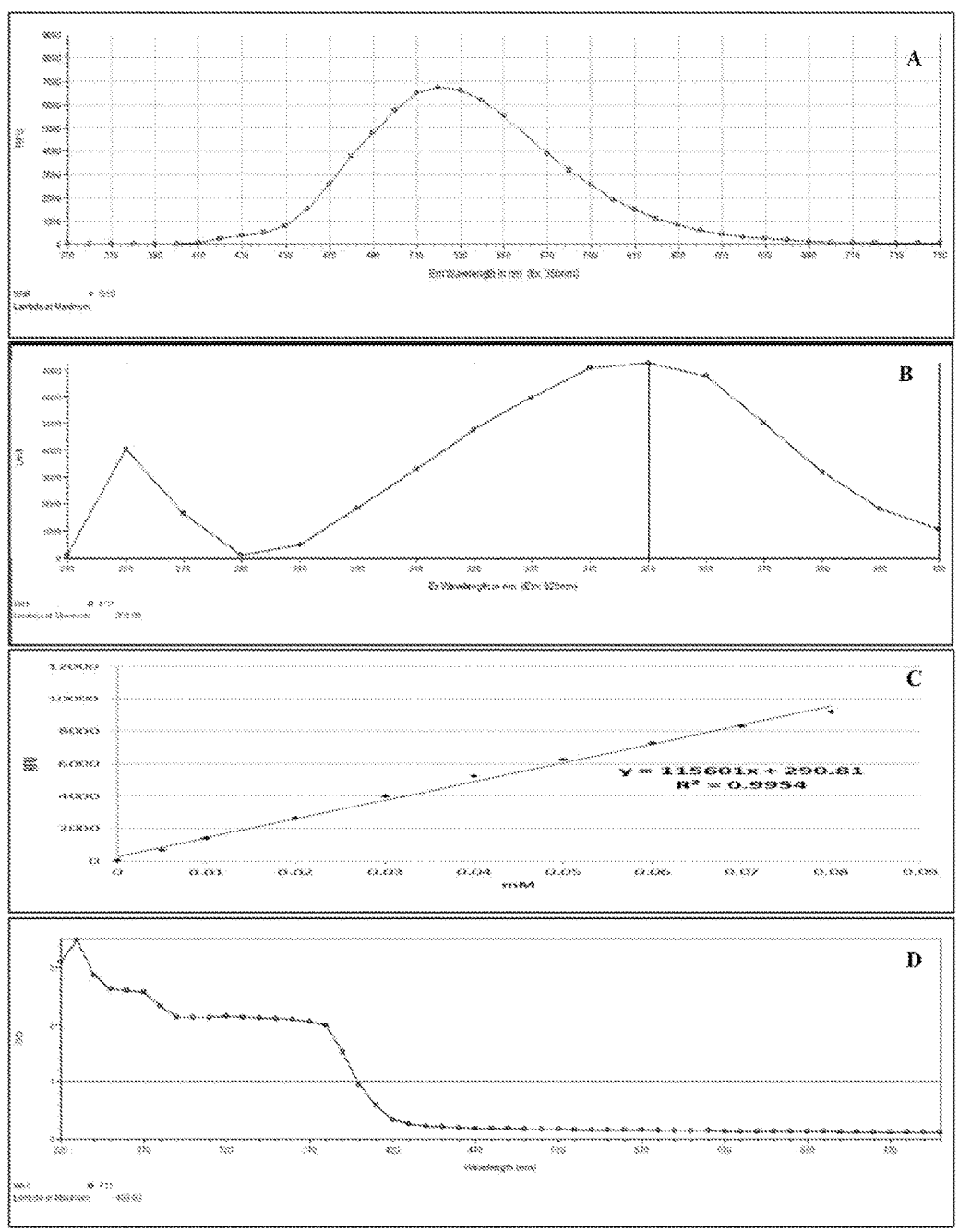
FIG. 9 includes graphs illustrating the fluorescence response of DCYA. A) Emission spectrum ($\lambda_{EX}$ 350 nm) B) Excitation spectrum ($\lambda_{EM}$ 520 nm) for DCYA (62.5 $\mu$M in acetonitrile, 200 $\mu$L/well) C) Calibration curve for DCYA (averaged data of two different operators) D) absorbance profile of DCYA.

The fluorescent responses of DCYA and DCYA disulfide in ACN were investigated at different concentrations using 1-300 μL/well in a 96 microplate reader at room temperature. Pure acetonitrile was used as a solvent control. The optimum excitation and emission wavelength combination was determined by performing excitation and emission scans. Both DCYA and its disulfide were found to have excitation and emission maxima at 350 and 520 nm, respectively, regardless of test concentration. At these wavelengths, no solvent interference was observed. However, 1.5-3.0% loss of fluorescence response was observed for micromolar solutions of DCYA after 3 h at room temperature. A linear response for DCYA was observed between 5-80 μM (10-160 nmol/well) concentrations with a $R^2=0.995$. Fluorescent emission spectrum and calibration curves for DCYA are provided in FIG. 9.

Solvent Effect.

Several solvent systems were tested, including the polar aprotic solvents, ACN and DMSO along with chlorinated solvents. Even though dimethyl sulfoxide and chloroform are known to be suitable solvents for nucleophilic additions, they were excluded because of issues with evaporation, pro-oxidation and interference with the spectrophotometric assay. Acetonitrile was thus chosen as the preferred solvent because of its low oxidative effect on DCYA and adequate solvent strength. The majority of the electrophilic compounds are highly hydrophobic in nature and the use of organic solvents minimize the risk of drowning-out effects.[72] The use of a two-solvent system has been previously suggested[12, 15, 48] but care should be taken in the comparison of results obtained in different solutions, because the solvent may have a strong influence on the extent of reaction. In some cases, especially with DMSO, the possibility of a pro-oxidization effect should be taken into account, as it may dramatically affect the quantification of the test compound.[51]

Catalysis and the Role of Controls.

Figure 10:
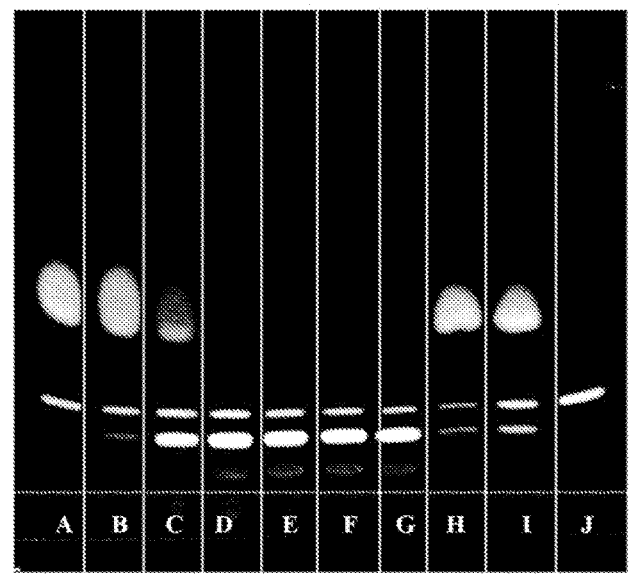
FIG. 10 includes UV$_{366}$ (fluorescence profile in the presence of different catalyst conditions using TLC experiments. The catalyst effect on the DCYA addition to parthenolide (P). A) DCYA standard; B-D) DBN 0.1, 0.2 and 0.4 equiv., respectively; E-G) Buffer pH 10 5 $\mu$L, 10 $\mu$L and 20 $\mu$L, respectively; H) 20 μL Buffer pH 7; I) Control DCYA+P without buffer; J) (DCYA)$_2$ standard. R$_f$ DCYA=0.33, DCYA disulfide=0.18, DCYA-P adduct=0.11. TLC in Silica gel, 0.8% MeOH in CHCl$_3$.
Figure 11:
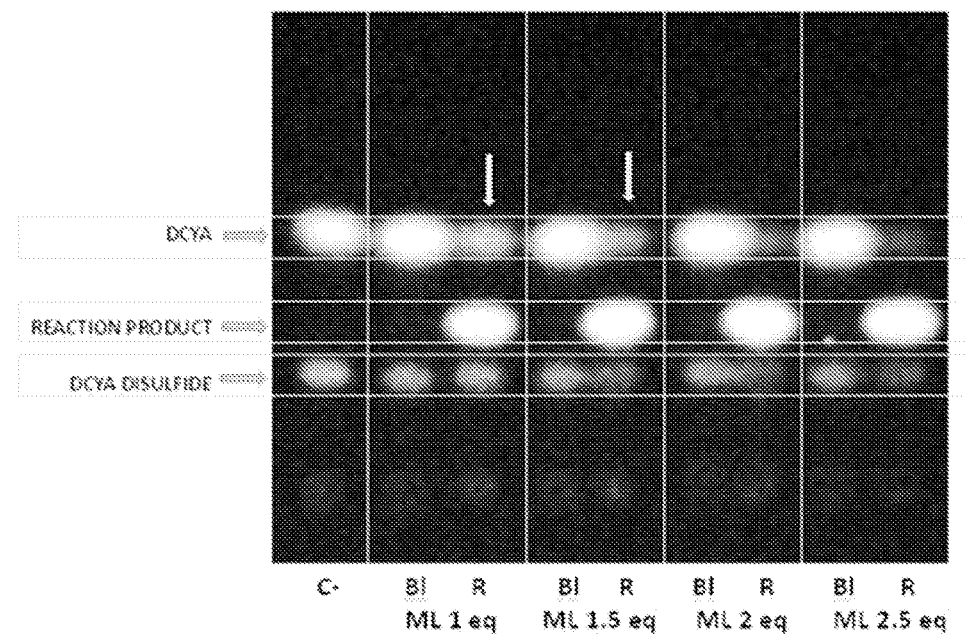
FIG. 11 shows the Thin Layer Chromatographic visualization for the effect of electrophile (ML) concentration on the nucleophile, DCYA after 20 minutes of incubation.
Figure 12:
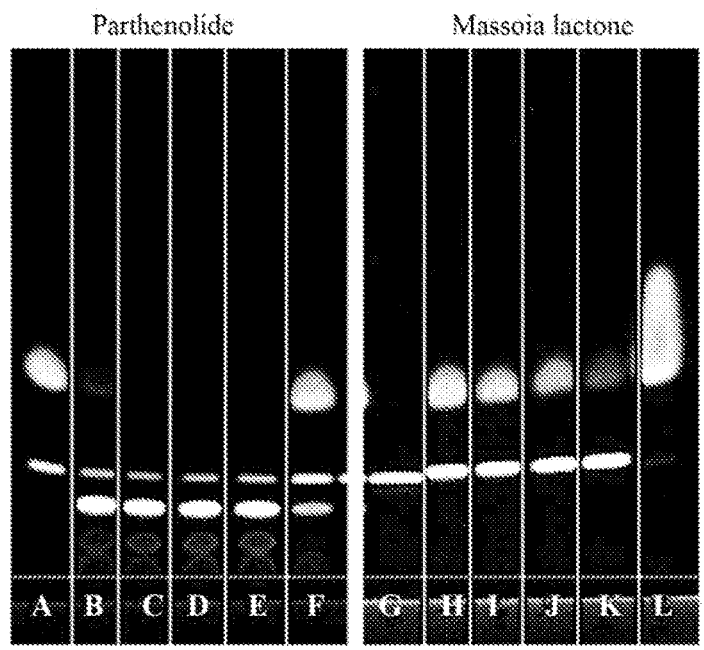
FIG. 12 includes images showing TLC UV$_{366}$ profile of Michael reactions between DCYA and parthenolide (P, left) or *Massoia* lactone (ML, right). The reactions were carried on in the presence of 20 μL buffer pH 10. A) DCYA standard; B-E) DCYA+1, 1.5, 2 and 2.5 equiv. of P respectively; F) Control DCYA+P without buffer; G) Standard (DCYA)$_2$; H-K) Reaction of DCYA with 1, 1.5, 2 and 2.5 equiv. of ML; L) Control DCYA+ML without buffer. TLC in Silica gel, eluent 0.8% MeOH in CHCl$_3$.
Figure 13:
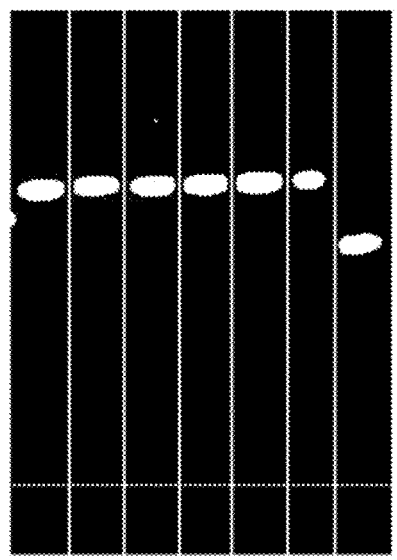
FIG. 13 includes images showing TLC UV$_{366}$ profile of Michael reactions between DCYA and Coumarin (COUM) in the presence of 20 μL pH 10 buffer. A) Control DCYA+COUM without buffer; B-E) Reaction of DCYA with 1, 1.5, 2 and 2.5 equiv. COUM respectively; F) DCYA standard; G) (DCYA)$_2$ standard. TLC stationary phase silica gel, eluent 40% acetone in hexane.

Because the reactivity of DCYA is dependent on the activation of the thiol by a base catalyst, the reaction rate in the presence of organic or inorganic bases was examined. The known sensitizer parthenolide (P), the small lipophilic natural terpene massoia lactone (ML) and the non-sensitizer coumarin (COUM) were chosen as model electrophiles to determine the degree of reaction. The organic base 1,5-diazabicyclo[4.3.0]non-5-ene (DBN) (pKa 13.5) and aqueous pH 10 buffer gave comparable results in preliminary studies, providing adequate conditions for activation of the thiol and further addition with test compounds. Parameters, such as concentration of the electrophile, catalyst, dilutions, and the incubation time, were further optimized for the fluorescence assay. To gain some insights on the influence of each parameter, thin-layer-chromatography experiments were conducted as a pictographic aid. Concentrations of DBN from 0.1 to 0.2 equiv. were insufficient to catalyze a complete conversion of parthenolide under the chosen conditions (FIG. 10), while higher conversion was obtained with 0.4 equiv. DBN or with pH 10 buffer. No substantial adduct was observed when pH 7 buffer was used. The same buffer conditions were further explored in the fluorescence assays in microplates after optimization of the thiol scavenging conditions. In order to calculate the net fluorescence derived from DCYA adducts, positive and negative controls were included (Table 3; experimental procedure). No DCYA mize the competition between auto-dimerization [(DCYA)$_2$] and nucleophilic addition, the reaction time and the electrophile:nucleophile stoichiometry were optimized. Massoia lactone at different concentrations was used to monitor the progress of the reaction by TLC (FIG. 11). In the presence of the electrophile, the formation of DCYA-ML adduct was dominant with negligible formation of (DCYA)$_2$. In the presence of strong electrophiles, such as parthenolide (P), the reaction product was dominant at the lower concentration tested (1 equiv.), while only a partial reaction was achieved in the presence of ML (FIG. 12). In the case of a non-sensitizer (COUM, FIG. 13), no reaction adduct was observed at the concentrations tested (Table 5). In order to adequately discriminate between compounds with variable electrophilic strength, the assay was optimized using 2 equivalents of electrophile. Higher concentrations may give an overestimation of reactivity for moderate electrophiles, while lower concentrations may negatively affect the sensitivity of the method, especially in the presence of weakly reactive compounds.

TABLE 5

Example of fluorescence response (average of 9 readings) for Massoia Lactone (ML), Parthenolide (P) and Coumarin (COUM).

| Sample | RFU | Sample | RFU | Sample | RFU | Sample | RFU |
|---|---|---|---|---|---|---|---|
| PC | 6823.559 | ML Bl | 7047.174 | P Bl | 7066.668 | COUM Bl | 6856.485 |
| NC | 1848.894 | ML R | 6064.127 | P R | 6865.723 | COUM R | 1996.775 |

PC = Positive Control,
NC = Negative Control,
Bl = Blank,
R = Reaction.

activation was expected in the absence of catalyst (PC). The neutral thiol should not react with the resin scavenger and the maximum recovery fluorescence in the supernatant was observed. In the negative control, DCYA and its conjugate base, DCYA$^-$ will be in equilibrium. The resulting thiolate will bind to the scavenger resin, and no fluorescent species should remain in the solution. The residual fluorescence read in the NC was used to calculate the background interference in the absence of any reaction. The PC and NC reactions were treated with an excess of maleimide resin, and diluted so that the fluorescence reading would be within the linear range of the calibration curve. Ideally, lower NC/PC ratios are desirable. As shown in Table 4. DBN concentrations up to 0.4 equiv. were insufficient to promote scavenging efficiency, whereas a better scavenging effect was obtained with 16% (v/v) pH 10 buffer.

TABLE 4

Effect of catalyst concentration in the diluted conditions for microplate assay.

| | NC | PC | NC/PC |
|---|---|---|---|
| DBN 10% | 6626 | 7126 | 0.93 |
| DBN 20% | 6255 | 7024 | 0.89 |
| DBN 40% | 5105 | 6228 | 0.82 |
| Buffer (pH 10) 10% | 2488 | 6648 | 0.37 |
| Buffer (pH 10) 16% | 1320 | 6209 | 0.21 |

NC = Negative control,
PC = Positive control.
Values reported are in fluorescence unit (RFU). The negative control represents the a specific spectrophotometric response (related to the amount of side reaction) obtained as a baseline. The reaction conditions must be optimized to give the lowest ratio NC/PC.

Electrophile Stoichiometry.

The reaction time is a critical factor, since thiols are easily oxidized to disulfides in basic conditions. In order to mini- Nucleophile Scavenger.

In order to selectively quantitate the fluorescent response of the DCYA-electrophile adduct, the unreacted thiolate (DCYA$^-$) must be efficiently removed from the solution (FIG. 8). This result can be achieved using a specific polymer-supported scavenger. Under optimum conditions, the DCYA$^-$ species will bind to the scavenger, while the DCYA-electrophile adduct will remain in solution. Maleimide supported on silica is here reported as an example of scavenger. Maleimide resin was found to readily and selectively bind to DCYA$^-$ under the chosen conditions. The effectiveness of the scavenger was also pH dependent, and optimum conditions were determined using 10-200 mmol equiv. of maleimide resin in the presence of 5-50% v/v aqueous pH 10 buffer (Table 4). Incubation period of 5-300 min was found to be sufficient to obtain a maximum scavenging effect.

Controls.

A positive control (PC) and negative control (NC) were included in each sample set to calculate the maximum (PC) and minimum (NC) fluorescence response (Table 3). A comparison between solutions of DCYA with or without incubation with the resin were analyzed, and a recovery of greater than 95% was obtained for the PC under the tested conditions. The "blank" (Bl) reading was obtained by combining the electrophile with DCYA without any catalyst. In these conditions, no reaction should occur and the fluorescence reading should be close to the positive control if no electrophile interference is observed. The reaction (R) readings were performed by mixing equal volumes of electrophile and DCYA in the presence of the pH 10 buffer. Reactive sensitizers generated higher fluorescence responses. All the controls and the reactions were performed in triplicate and each plate was read at least three times, thus obtaining a total of 9 readings per sample.

Data Analysis.

A minimum of 9 readings were averaged per sample, and an example of the raw data obtained is reported in Table 5. The degree of reaction was calculated based on the comparison between the reaction response and the controls according to the formula $$RI = 100\left\{\frac{Bl - R}{PC - NC} - \frac{PC - BL}{PC}\right\}$$

where the reactivity index RI is proportional to the electrophilic reactivity of the candidate sensitizer. Caution should be taken when using the RI value to determine the extent of reaction: although a direct relationship between the extent of reaction and the RI exists, RI of 100 does not necessarily mean 100% reaction.

An example of results from fluorescence reading endpoints is herein reported using DCYA and Massoia lactone (Table 6). Averaged data are reported for the 9 registered values for each sample. From the obtained data, RI will be calculated as:

$$RI = 100 \times \left\{1 - \frac{7047 - 6064}{6824 - 1849} - \frac{6824 - 7047}{6824}\right\}$$

thus giving a $RI = 83.5$

Figures 14A, 14B, 14C, 14D:
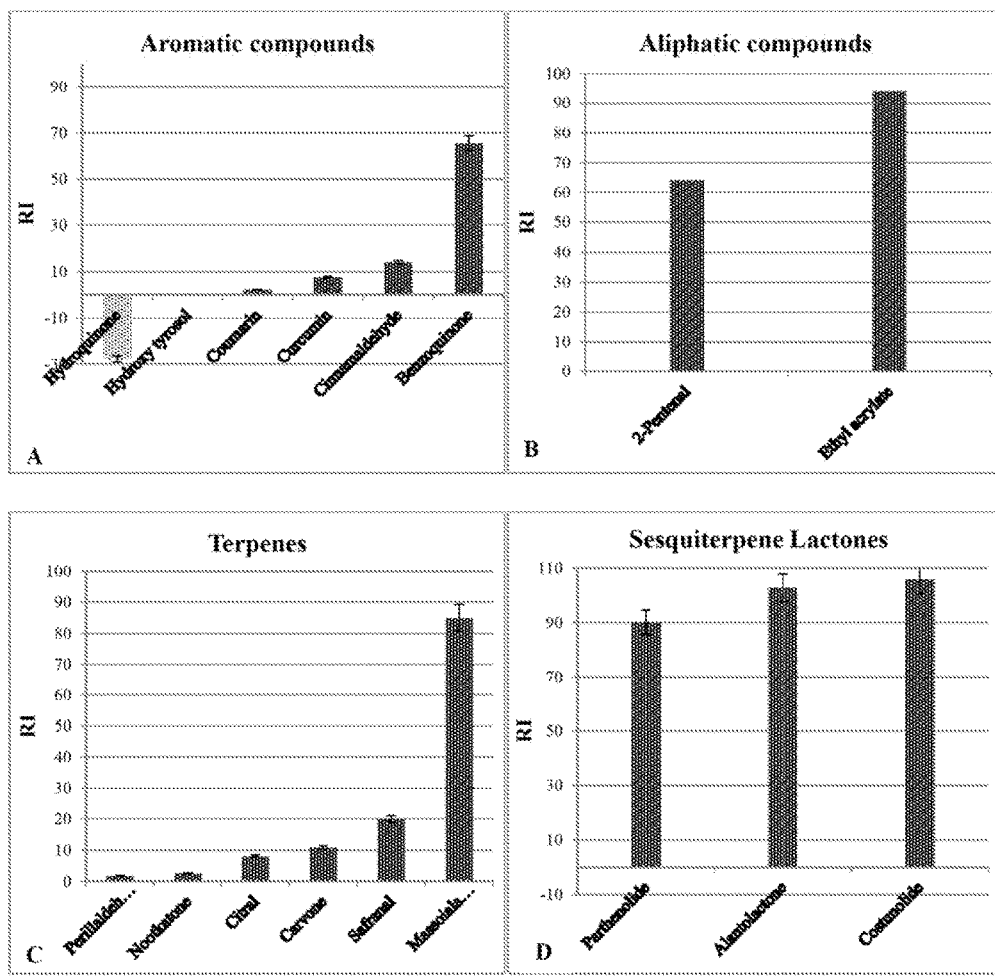
FIG. 14 shows the experimental results for microplate spectrophotometric method using fluorescence end-point detection after 20 min incubation of potential sensitizers with fluorescent nucleophile.

In order to compare the performance of the fluorescence spectrophotometric assay with existing methods of skin sensitization assessment, a set of known sensitizers was investigated. The list includes 36 natural and synthetic compounds covering a range of diverse mechanistic domains and sensitization potential from the "Silver-list".[64] Compounds lacking requisite mechanistic domains (such as hydroquinone or cinnamyl alcohol)[73] have also been included in the list, but they have been excluded from the statistical analysis because the impossibility of identifying pre- or pro-sensitizers using in chemico approaches is a known limitation of existing methods. The results of the DCYA assay are presented in Table 7 along with Cys-DPRA results from the literature. For data comparison purposes with the Cys-DPRA (which are given as percentage of remaining peptide), results are given as 100-RI. As expected, the putative pre- or pro-haptens[70] hydroquinone, resorcinol or hydroxytyrosol, were found to be non-reactive in both Cys-DPRA and DCYA assays. For comparison purposes, some of the select sensitizers' results are presented in FIG. 14. The cyclic anhydride, 1,2-cyclohexanedicarboxylic anhydride, is a known respiratory allergen with higher selectivity for lysine than cysteine.[74] Occurrence of contact urticaria to cyclic anhydrides is rare compare to the widespread cases of respiratory allergy although cases of contact allergy have been reported as occupational hazards.[75] In the case of p-benzoquinone (BQ), the candidate compound was correctly identified as a sensitizer[54] but the potency has been underestimated because of known and unavoidable issues with BQ. Lilial was found non-reactive in the DCYA assay, and these finding correlated with the KeratinoSens™ data.

TABLE 6

Example of results from microplate readings for end-point fluorescence assay using DCYA and massoia lactone.

| | 1 | 2 | 3 | | 4 | 5 | 6 |
|---|---|---|---|---|---|---|---|
| | | | Reading 1 | | | | |
| A | 6696.97 | 6592.075 | 7154.477 | C | 7193.987 | 6941.313 | 7095.217 |
| B | 1747.128 | 1854.001 | 1970.193 | D | 5849.637 | 6495.332 | 6025.181 |
| | | | Reading 2 | | | | |
| A | 6805.548 | 6573.46 | 7099.189 | C | 7143.046 | 6900.74 | 7081.942 |
| B | 1764.078 | 1836.573 | 1936.781 | D | 5802.452 | 6407.07 | 5922.368 |
| | | | Reading 3 | | | | |
| A | 6809.528 | 6578.34 | 7102.443 | C | 7133.007 | 6884.451 | 7050.862 |
| B | 1757.252 | 1834.257 | 1939.781 | D | 5773.022 | 6392.737 | 5909.346 |
| | | | Average | | | | |
| | 6824 | | | C | 7047 | | |
| | 1849 | | | D | 6064 | | |

Values are reported in RFU.
A = Positive control (PC);
B = Nagative control (NC);
C = ML blank (Bl)
D = ML Reaction (R).

Discussion.

In the current method, a dansyl cysteamine derivative was used as non-limiting example of model nucleophile to demonstrate the applicability of the disclosed method in skin sensitization risk assessment. The disclosed spectrophotometric method, 'DCYA assay', aimed at the identification and classification of potential skin sensitizers based on their electrophilic reactivity toward a model fluorescent thiol is provided.

Bromo butane and benzaldehyde were classified as non-reactive with the DCYA method, while a minimal reaction was found with Cys-DPRA. Bromo butane is considered a false positive in Cys-DPRA. However, a minor DCYA adduct with bromo butane was observed after 24 h of incubation. This case exemplifies the risk of overestimation of the nucleophile depletion during long incubation periods. In the case of benzaldehyde, no DCYA adducts were identified, and the possibility of over-estimation due to the pro-oxidant effect of benzaldehyde should be considered.

TABLE 7

Reactivity classification of known sensitizers in DCYA assay and comparison with reported results for existing methods.

| CHEMICAL | CAS# | DCYA 100-RI | Cys-DPRA % Pept. remain. | Keratino-Sens™ EC3 (µM) | LLNA EC3[‡] | Comments |
|---|---|---|---|---|---|---|
| Diphenyl cyclopropenone | 886-38-4 | 96.3 | 1.2 | 1.84 | 0.003 | Ref.[64] |
| p-Benzoquinone | 106-51-4 | 34.5 | 1 | 32.77 | 0.01 | Ref.[64] |
| 1-Chloro-2,4-dinitrobenzene | 97-00-7 | 131.7 | 0 | 3.89 | 0.05 | Ref.[64] |
| p-Hydroquinone | 123-31-9 | 127.1 | 16.7 | 51.29 | 0.11 | Ref.[64] [a] |
| Propionolactone | 57-57-8 | 64.9 | n.a. | n.a. | 0.2 | Ref.[13,64] |
| 3-Hydroxytyrosol | 10597-60-1 | 97.2 | n.a. | n.a. | 0.6 | [70a] |
| 1,2-Cyclohexanedicarboxylic anhydride | 85-42-7 | 104.6 | 84.3 | >2000 | 0.84 | Ref.[64b] |
| 2-Methyl-4-isothiazolin-3-one | 2682-20-4 | 16.4 | 2.1 | 29.56 | 1.9 | Ref.[64] |
| Cinnamaldehyde | 14371-10-9 | 85.1 | 29.4 | 63.94 | 3 | Ref.[64] |
| 2,4-Heptadienal | 3/5/4313 | 54.1 | 2.7 | 21.91 | 4 | Ref.[64] |
| 4-Hex-3-en-one | 2497-21-4 | 2.8 | n.a. | n.a. | 4.2 | [44] |
| Squaric acid | 2892-51-5 | 91.1 | 53.1 | >2000 | 4.3 | Ref.[64] |
| trans-2-Hexenal | 6728-26-3 | 29.9 | 2.1 | 374.57 | 5.5 | Ref.[64] |
| Resorcinol | 108-46-3 | 103.5 | 98.4 | >2000 | 5.5 | Ref.[64] |
| Diethyl maleate | 141-05-9 | −8.84 | 0 | 82.85 | 5.8 | Ref.[64] |
| Safranal | 116-26-7 | 82.9 | 9.5 | n.a. | 7.5 | Ref.[60,64] |
| Perillaldehyde | 2111-75-3 | 95.8 | 68.1 | 61.85 | 8.1 | Ref.[64] |
| Citral | 5392-40-5 | 88.8 | 14.3 | 67.36 | 9.2 | Ref.[64] |
| Farnesal | 502-67-0 | 92.85 | 83.6 | >2000 | 12 | Ref.[64] |
| L-Carvone | 6485-40-1 | 88.4 | n.a. | n.a. | 13 | Ref.[64] |
| Oxalic acid | 144-62-7 | 89.4 | 99.1 | >2000 | 15 | Ref.[64] |
| Benzyl benzoate | 120-51-4 | 110.6 | 99.8 | 142.47 | 17 | Ref.[64] |
| Lilial | 80-54-6 | 98.9 | 86 | >2000 | 19 | Ref.[64] |
| Cinnamyl alcohol | 104-54-1 | 105.0 | 100 | >2000 | 21 | Ref.[64] |
| cis-6-Nonenal | 2277-19-2 | 107.3 | 92 | 687.67 | 23 | Ref.[64] |
| 5-Methyl-2,3-hexanedione | 13706-86-0 | 90.3 | 74.2 | 332.21 | 26 | Ref.[64] |
| Ethyl acrylate | 140-88-5 | −0.7 | 3.6 | 231.19 | 28 | Ref.[64c] |
| Aniline | 62-53-3 | 107.0 | 100 | >2000 | 89 | Ref.[64] |
| 1-Bromobutane | 109-65-9 | 100.0 | 86.2 | >2000 | NC | Ref.[64] |
| Vanillin | 121-33-5 | 106.4 | 96.8 | >2000 | NC | Ref.[64] |
| Tartaric acid | 87-69-4 | 100.7 | 96.2 | >2000 | NC | Ref.[64] |
| Chlorobenzene | 108-90-7 | 97.8 | 99.6 | >2000 | NC | Ref.[64] |
| Lactic acid | 50-21-5 | 100.1 | 100 | >2000 | NC | Ref.[64] |
| Salicylic acid | 69-72-7 | 106.9 | 96.5 | >2000 | NC | Ref.[64] |
| Coumarin | 91-64-5 | 97.2 | 99 | 479.96 | NC | Ref.[64] |
| Benzaldehyde | 100-52-7 | 98.1 | 92.8 | >2000 | NC | Ref.[64] |

[a]Putative pre/pro-hapten;
[b]Selective towards Lys-DPRA;
[c]False negative in LLNA Based on 100-RI values for the tested compounds in DCYA method, a binary classification was obtained (Table 8) where DCYA and Cys-DPRA results were classified as true positive, true negative, false positive and false negatives.

TABLE 8

Binary classification of potential sensitizers in DCYA and DPRA.

| CHEIMICAL | CAS # | DCYA | | | | Cys-DPRA | | | |
|---|---|---|---|---|---|---|---|---|---|
| | | TP | TN | FP | FN | TP | TN | FP | FN |
| Diphenyl cyclopropenone | 886-38-4 | 0 | 0 | 0 | 1 | 1 | 0 | 0 | 0 |
| p-Benzoquinone | 106-51-4 | 1 | 0 | 0 | 0 | 1 | 0 | 0 | 0 |
| 1-Chloro-2,4-dinitrobenzene | 97-00-7 | 0 | 0 | 0 | 1 | 1 | 0 | 0 | 0 |
| Propionolactone | 57-57-8 | 1 | 0 | 0 | 0 | n.a. | 0 | 0 | 0 |
| 2-Methyl-4-isothiazolin-3-one | 2682-20-4 | 1 | 0 | 0 | 0 | 1 | 0 | 0 | 0 |
| Cinnamaldehyde | 14371-10-9 | 1 | 0 | 0 | 0 | 1 | 0 | 0 | 0 |
| 2,4-Heptadienal | 4313-03-5 | 1 | 0 | 0 | 0 | 1 | 0 | 0 | 0 |
| 4-Hex-3-en-one | 2497-21-4 | 1 | 0 | 0 | 0 | n.a. | 0 | 0 | 0 |
| Squaric acid | 2892-51-5 | 0 | 0 | 1 | 0 | 1 | 0 | 0 | 0 |
| trans-2-Hexenal | 6728-26-3 | 1 | 0 | 0 | 0 | 1 | 0 | 0 | 0 |
| Diethyl maleate | 141-05-9 | 1 | 0 | 0 | 0 | 1 | 0 | 0 | 0 |
| Safranal | 116-26-7 | 1 | 0 | 0 | 0 | 1 | 0 | 0 | 0 |

TABLE 8-continued

Binary classification of potential sensitizers in DCYA and DPRA.

| | | DCYA | | | | Cys-DPRA | | | |
|---|---|---|---|---|---|---|---|---|---|
| CHEIMICAL | CAS # | TP | TN | FP | FN | TP | TN | FP | FN |
| Perillaldehyde | 2111-75-3 | 0 | 0 | 0 | 1 | 1 | 0 | 0 | 0 |
| Citral | 5392-40-5 | 1 | 0 | 0 | 0 | 1 | 0 | 0 | 0 |
| Farnesal | 502-67-0 | 1 | 0 | 0 | 0 | 1 | 0 | 0 | 0 |
| L-Carvone | 6485-40-1 | 1 | 0 | 0 | 0 | n.a. | 0 | 0 | 0 |
| Oxalic acid | 144-62-7 | 0 | 0 | 1 | 0 | 0 | 1 | 0 | 0 |
| Benzyl benzoate | 120-51-4 | 0 | 1 | 0 | 0 | 0 | 1 | 0 | 0 |
| Lilial | 80-54-6 | 0 | 0 | 0 | 1 | 0 | 0 | 1 | 0 |
| cis-6-Nonenal | 2277-19-2 | 0 | 0 | 0 | 1 | 1 | 0 | 0 | 0 |
| 5-Methyl-2,3-hexanedione | 13706-86-0 | 1 | 0 | 0 | 0 | 1 | 0 | 0 | 0 |
| Ethyl acrylate | 140-88-5 | 1 | 0 | 0 | 0 | 1 | 0 | 0 | 0 |
| 1-Bromobutane | 109-65-9 | 0 | 1 | 0 | 0 | 0 | 0 | 1 | 0 |
| Vanillin | 121-33-5 | 0 | 1 | 0 | 0 | 0 | 1 | 0 | 0 |
| Tartaric acid | 87-69-4 | 0 | 1 | 0 | 0 | 0 | 1 | 0 | 0 |
| Chlorobenzene | 108-90-7 | 0 | 1 | 0 | 0 | 0 | 1 | 0 | 0 |
| Lactic acid | 50-21-5 | 0 | 1 | 0 | 0 | 0 | 1 | 0 | 0 |
| Salicylic acid | 69-72-7 | 0 | 1 | 0 | 0 | 0 | 1 | 0 | 0 |
| Coumarin | 91-64-5 | 0 | 1 | 0 | 0 | 0 | 1 | 0 | 0 |
| Benzaldehyde | 100-52-7 | 0 | 1 | 0 | 0 | 0 | 0 | 1 | 0 |
| Costunolide | 553-21-9 | 1 | 0 | 0 | 0 | n.a. | n.a. | n.a. | n.a. |
| Alantolactone | 546-43-0 | 1 | 0 | 0 | 0 | n.a. | n.a. | n.a. | n.a. |
| Parthenolide | 20554-84-1 | 1 | 0 | 0 | 0 | n.a. | n.a. | n.a. | n.a. |
| Total | | 17 | 9 | 2 | 5 | 16 | 8 | 3 | 0 |

Yes = 1,
No = 0

Cooper statistical analysis was performed to compare DCYA and Cys-DPRA results (Table 9). Chemicals with an RI-100<95 were classified as positive skin sensitizers in DCYA assay (Table 7). The DCYA and Cys-DPRA methods gave similar results in terms of accuracy (78.8% and 88.9%, respectively) for the limited set of sensitizers tested. The main discrepancies between the two tests appeared with regard to potency categorization. A tendency to overestimation of the potency of moderate electrophiles in the Cys-DPRA was found, especially with potential pro-oxidizers. This observation was confirmed by the higher number of false positive in Cys-DPRA than DCYA. On the other hand, some weak and moderate compounds were underestimated in potency using the DCYA method, especially in the case of sensitizers with very weak or borderline reactivity. The majority of strong electrophiles displayed an RI-100 value <20, whereas moderate electrophiles measured in the range 80 to 20. Non-sensitizers registered on average an RI-100 value of >95.

TABLE 9

Copper statistics for DCYA and DPRA assays.

| | DCYA | DPRA |
|---|---|---|
| Accuracy | 78.8 | 88.9 |
| Sensitivity | 77.3 | 100.0 |
| Specificity | 81.8 | 72.7 |
| N | 33 | 27 |

Along with the known set of sensitizers, 6 compounds excluded from the "Silver-list" were investigated and their potential reactivity was evaluated (Table 10). The three lactones (costunolide, parthenolide and alantolactone) are among the most common contact allergens isolated from plants,[65, 68, 76] and they are constituents of the sesquiterpene lactone mix[66] and the Compositae mix used in clinical patch tests.[77] Costunolide, alantolactone and parthenolide were found to be equally strongly reactive. The small natural aldehyde t-2-pentenal was classified according to DCYA results as moderate reactive, with an RI-100 close to the homologous t-2-hexenal, which was also found as moderate sensitizer in LLNA.[62] Finally, the two volatile Michael acceptors ML and nootkatone were determined to have RI-100 values of 12.8 and 96.5, respectively.

TABLE 10

DCYA results for six chemicals with no in chemico evaluation.

| Chemical | CAS# | DCYA (100-RI) | Reference and comment |
|---|---|---|---|
| Costunolide | 553-21-9 | −8.5 | Ducombs, 1990[a] |
| Alantolactone | 546-43-0 | −6.7 | Ducombs, 1990[a] |
| Parthenolide | 20554-84-1 | 7.9 | Ducombs, 1990[a] |
| Massoia lactone | 51154-96-2 | 12.8 | — |
| trans-2-Pentenal | 1576-87-0 | 18.2 | — |
| Nootkatone | 4674-50-4 | 96.5 | — |

[a]Positive in human patch tests

The high sensitivity, specificity and shorter reaction time of the model reaction enabled the development of a user-friendly procedure suitable for high-throughput screenings using a multidetection microplate reader. The proposed approach rely on the direct quantification of the reaction adducts in contrast to existing in chemico methods. The reaction conditions have been optimized to overcome the major limitations of existing techniques, such as low throughput, solubility issues and oxidative side reactions. Thirty-six candidates previously classified as sensitizers by Local Lymph Node Assay, Direct-Peptide Reactivity Assay or KeratinoSens™ were tested. In addition to the known sensitizers, six other natural products were analyzed and the sesquiterpene lactones, costunolide, alantolactone and parthenolide were correctly identified as strong sensitizers.

Example 3: Screening of Complex Mixtures Including Phytochemical Crude Extracts The majority of the in chemico as well as in vive and in silico methods dealing with skin sensitizer have been optimized for quantification of pure compounds. Very little information is available concerning the potential sensitization by complex mixtures. Recently, Andres et al.[47] explored the possibility of using the KeratinoSens™ assay for plant extracts, but the applicability of the assay must be limited to mixtures that do not pose a cytotoxicity problem for the cell line used in the screening. Analysis of complex mixtures represents an important task in skin toxicology, since almost all the clinical cases can be related to topical use of multiple compounds, such as drug formulations, cosmetics or plant materials. Physicians mostly deal with severe skin allergy and can often identify formulations responsible for the adverse effect but extra efforts are required to determine how many agents can actually cause dermatitis. Only rarely does skin come into contact with pure compounds, and more complex interaction between one or more compound can elicit adverse effects otherwise not predictable by screening of the individual components. For example, if one compound acts as a pre/pro-hapten and require some kind of activation to the true sensitizer, other compounds may be able to accelerate or inhibit this process. Precisely, anti-oxidant compounds may prevent the chemical conversion of pre-haptens, thus contributing to an overall minor sensitization potential compared to the same pre-haptens evaluated in the absence of such anti-oxidants. The development of toxicological screening methods that can identify potential skin sensitizers in mixtures is therefore essential.

Materials and Methods

Plant Extraction.

Dry *Magnolia grandiflora* leaves (17.9 g) were extracted in 10 volumes of $CH_2Cl_2$ for 30 min in a sonicator. The solvent was evaporated, yielding 0.68 g of crude extract (3.8% w/w). Three hundred mg was purified by chromatography on RP-$C_{18}$ with MeOH to remove the chlorophylls and pigments (obtained fraction was 71.4 mg, yield 21.6% w/w). German chamomile (*Matricaria recutita*) and Roman chamomile (*Chamaemelum nobile*) flower heads were extracted in hexane under sonication for 30 min.

Spectroscopy.

The presently disclosed example relates to methods detecting, categorizing potential skin sensitizers from plant/botanical extracts using nuclear magnetic resonance (NMR) spectroscopy, microplate spectrophotometry and/or other spectroscopic methods. All these methods can be used as stand-alone or in combination for direct quantification of hapten adducts with minimal side reactions. As non-limiting example, a microplate spectrophotometric assay was demonstrated for the detection and classification of potential plant extracts as a sensitizers.

In the following example, the DCYA method was applied to the screening of plant extracts from three species known to cause skin allergy. The candidate plants were *magnolia* (*Magnolia grandiflora*), German chamomile (GC) (*Matricaria recutita*) and Roman chamomile (RC) (*Chamaemelum nubile*). Magnolia leaves are known for their sesquiterpene lactones content.[78] In the case of German and Roman chamomile, samples from an in house collection of both plants and their enriched fractions were previously tested by KeratinoSens™ (Table 11). The same fractions were also tested by DCYA assay to investigate the correlation between the two tests.

TABLE 11

Comparison of DCYA assay and KeratinoSens™ analysis of German and Roman chamomile extracts and one enriched fraction from German chamomile.

|  | DCYA RI | KeratinoSens™ EC1.5 (µg/mL)[#] |
|---|---|---|
| RC Extract | 45.5 | 0.718 |
| GC Extract | 39.8 | 3.29 |
| GC Fraction | 20.6 | 24.8 |

[#]Institute for In Vitro Sciences, Inc, Gaithersburg, MD, USA

A Quantitative comparison of the results is challenging because of the differences in the end-points evaluated in the two tests. KeratinoSens™ results are expressed as EC1.5, which refers to the minimum concentration of compound able to elicit gene induction >1.5 times compared to controls (DMSO). Reactivity Index (RI), instead, is directly related to the amount of product forming. Thus, a high RI or low EC1.5 indicates the presence of a potential sensitizer.

All three plants were classified as potential sensitizers in the microplate spectrophotometric method, even using crude extracts. Crude extracts are usually chemically complex, containing a huge variety of classes of compounds. The presence of known interferences (ex. pigments, polyphenols) is common when testing for biological activity and constitutes a major drawback when working with crude mixtures. Plant extracts are usually characterized by a high number of compounds present in very low concentration. This is a major challenge for screenings, which have to be proven sensitive in order to detect low amount of compound and selective enough to avoid false negative results.

Figure 15:
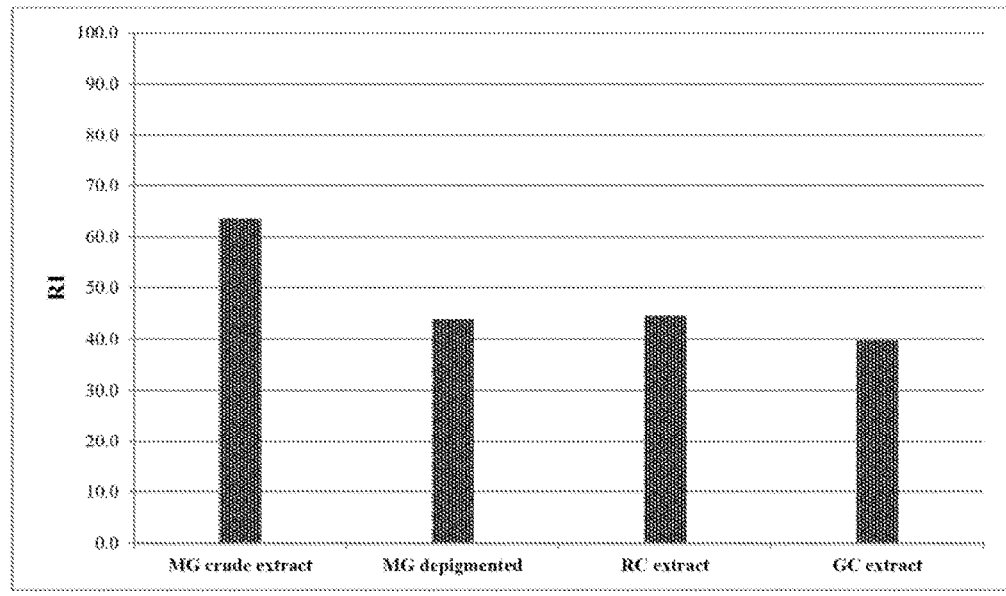
FIG. 15 shows the calculated RI for crude extracts using microplate spectrophotometric method. From left to right: *M. grandiflora* total extract; *M. grandiflora* enriched fraction after removal of chlorophyll; Roman chamomile crude extract; German chamomile crude extract.

The TLC analysis from *Magnolia grandiflora* crude extract and depigmented fraction showed no significant interferences from pigments and chlorophyll. Both the crude extract and the enriched fraction were found to have sensitization potential. TLC analyses were performed using commercial parthenolide as a reference. The TLC assay clearly showed that parthenolide was present in the crude extract and was one of the reactive species. Moreover, several minor candidates were also identified, confirming that parthenolide is not a unique sensitizer in *M. grandiflora* leaves (FIG. 15).

Figure 16:
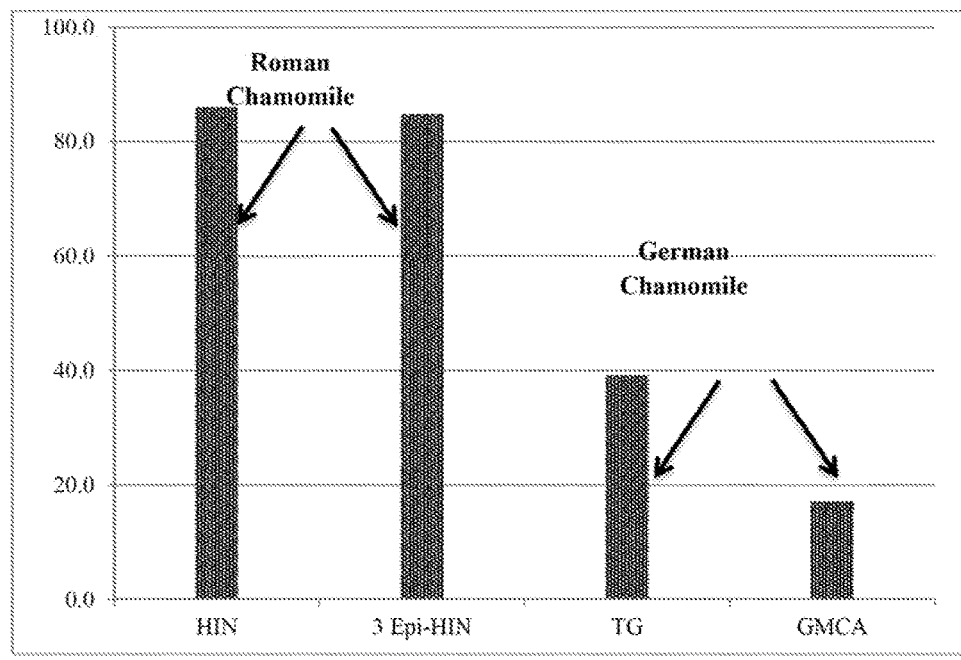
FIG. 16 provides an evaluation of pure compounds from chamomile using microplate spectrophotometric method. HIN=hydroxyisonobilin: 3 Epi-HIN=3 Epi-hydroxyisonobilin; TG=tonghaosu; GMCA=glucomethoxycinnamic acid.

Further examples were provided by chamomile samples, which were authenticated and tested for sensitization properties using KeratinoSens™. Preliminary data from in vitro assays indicates that both plants extract and their enriched fractions possess some sensitization potential, with Roman chamomile (*Chamaemelum nobile*) being more allergenic than German (*Matricaria recutita*) chamomile. The same fractions were tested in the microplate spectrophotometric method. The data are in agreement with the KeratinoSens™ assay, and from the spectrophotometric method both crude extracts were identified as moderate sensitizers, with Roman chamomile more reactive than German chamomile. The major constituents from both chamomile plants were then isolated. Potential candidates for skin sensitization were identified in the polyacetylene tonghaosu and cinnamaldehyde derivatives cis- and trans-glucopyranosyloxy-4-methoxycinnamic acid (GMCA).[79] The main candidates in Roman chamomile were the germacranolides, hydroxyisonobilin and 3 epi-hydroxyisonobilin.[80] As shown in FIG. 16, both germacranolides were highly reactive in the spectrophotometric method, while cis- and trans-GMCA were classified as weak sensitizers. The polyacetylene tonghaosu was more reactive than the two aromatic compounds but less than the two lactones from Roman chamomile. The pure compounds have not been tested on KeratinoSens™ yet but data on crude mixture showed a good degree of correlation between KeratinoSens™ and the spectrophotometric results.

In conclusion, the proposed spectroscopic methods to detect their reactivity of model nucleophile selective for electrophilic compounds, provides a facile, sensitive, and direct assay for assessing skin sensitization potential of chemicals. Using this assay, several known sensitizers including complex mixtures have been classified, and several novel potential sensitizers originating from natural sources have been also identified. Furthermore, this assay opens the door to future high-throughput screenings in the identification of potential sensitizers from dyes, industrial chemicals, and personal care products including cosmetics. The utility of the spectroscopic approach has been exemplified using non limiting examples such as nuclear magnetic resonance and microplate spectrophotometric methods. Traditional methods based on LC-MS or indirect peptide depletion assay do not give any mechanistic information on the reactivity of these compounds, where identifying and classifying the type of reactivity could actually be crucial for risk assessment concerning skin sensitization. The proposed spectroscopic approach using a NMR method may provide very useful insight on the kinetics and mechanisms of reaction, which could be also used for improving in silico hazard assessment methods. The application of the spectroscopic method using a microplate spectrophotometric assay to direct quantify the reaction products using an end-point assay provide an additional example for the simultaneous screening of multiple compounds or mixtures of compounds, especially valuable when limited amount of samples or large chemical libraries has to be rapidly and inexpensively evaluated. The non-limiting applications exemplify the use of two different spectroscopic approaches to directly characterize the electrophilic potential of chemicals, an essential feature of skin sensitizers. The two described examples can be applied independently or in combination as they complement each other in the identification of potential skin sensitizers in pure preparations, complex natural extracts or commercial formulations. More importantly, to achieve the urgent need of replacement of animal tests, the two approaches here reported may serve as a novel tools in identification and classification of potential sensitizers in combination with other approaches as integrated testing strategy, to better represent the complex cascade of events underlying skin sensitization.

REFERENCES (1) Kimber, I., Basketter, D., Gerberick, G., Ryan, C., and Dearman, R. (2011) Chemical allergy: translating biology into hazard characterization. *Toxicol. Sci.* 120 *Suppl* 1. S238-S268.
(2) Magnusson, B., and Kligman, A. M. (1969) The identification of contact allergens by animal assay. The guinea pig maximization test. *J. Invest. Dermatol* 52, 268-276.
(3) Buehler, E. V. (1965) Delayed Contact Hypersensitivity in the Guinea Pig. *Arch. Dermatol.* 91, 171-175.
(4) (2009) ICCVAM. 2009. Recommended Performance Standards: Murine Local Lymph Node Assay. NIH Publication Number 09-7357. Research Triangle Park, N.C.: National Institute of Environmental Health Sciences. http://iccvam.niehs.nih.gov/methods/immunotox/ll-na_PerfStds.htm (Accessed on Jun. 12, 2014).
(5) Kimber, I., and Basketter, D. A. (1992) The murine local lymph node assay: a commentary on collaborative studies and new directions. *Food. Chem. Toxicol.* 30, 165-169.
(6) (2006) Regulation (EC) No 1907/2006—REACH: Registration, Evaluation, Authorisation and Restriction of Chemicals (REACH) and establishing a European Chemicals Agency.
(7) Van der Jagt, K., Munn, S., Tørsløv, J., and de Bruijn., J. (2004) Alternative approaches can reduce the use of test animals under REACH. *European Commission, Joint Research Centre, Report EUR* 21405.
(8) Hartung, T., and Rovida, C. (2009) Chemical regulators have overreached. *Nature* 460, 1080-1081.
(9) Ahlfors, S., Sterner, O., and Hansson, C. (2003) Reactivity of contact allergenic haptens to amino acid residues in a model carrier peptide, and characterization of formed peptide-hapten adducts. *Skin Pharmacol. Appl. Skin Physiol.* 16, 59-68.
(10) Aptula, A., and Roberts, D. (2006) Mechanistic applicability domains for nonanimal-based prediction of toxicological end points: general principles and application to reactive toxicity. *Chem. Res. Toxicol.* 19, 1097-1105.
(11) Gerberick, F., Aleksic, M., Basketter, D., Casati, S., Karlberg, A. T., Kern, P., Kimber, L., Lepoittevin. J. P., Natsch, A., Ovigne, J. M., Rovida, C., Sakaguchi, H., and Schultz, T. (2008) Chemical reactivity measurement and the predicitve identification of skin sensitisers. The report and recommendations of ECVAM Workshop 64. *Altern. Lab. Anim.* 36, 215-242.
(12) Gerberick, G., Ryan, C., Kern, P., Dearman, R., Kimber, I., Patlewicz, G., and Basketter, D. (2004) A chemical dataset for evaluation of alternative approaches to skin-sensitization testing. *Contact dermatitis* 50, 274-288.
(13) Gerberick, G., Vassallo, J., Bailey, R., Chancy, J., Morrall, S., and Lepoittevin, J.-P. (2004) Development of a peptide reactivity assay for screening contact allergens. *Toxicol. Sci.* 81, 332-343.
(14) Natsch, A., and Emter. R. (2008) Skin sensitizers induce antioxidant response element dependent genes: application to the in vitro testing of the sensitization potential of chemicals. *Toxicol. Sci.* 102, 110-119.
(15) Natsch, A., and Gfeller, H. (2008) LC-MS-based characterization of the peptide reactivity of chemicals to improve the in vitro prediction of the skin sensitization potential. *Toxicol. Sci.* 106, 464-478.
(16) Andreas, N., Caroline. B., Leslie, F., Frank, G., Kimberly, N., Allison, H., Heather, T., Robert, L., Stefan, O., Hendrik, R., Andreas, S., and Roger, E. (2011) The intra- and inter-laboratory reproducibility and predictivity of the KeratinoSens assay to predict skin sensitizers in vitro: results of a ring-study in five laboratories. *Toxicol. In Vitro* 25, 733-744.
(17) Natsch, A., Emter, R., Gfeller, H., Haupt, T., and Ellis, G. (2015) Predicting skin sensitizer potency based on in vitro data from KeratinoSens and kinetic peptide binding: Global vs. domain-based assessment. *Toxicol. Sci.,* 143, 319-332.
(18) OECD. (2015) Test No. 442D: In Vitro Skin Sensitisation. http://www.oecd-ilibrary.org/environment/test-no-442d-in-vitro-skin-sensitisation_9789264229822-en (Accessed on 10 Jun. 2015), OECD Publishing.
(19) OECD. (2015) Test No. 442C: In Chemico Skin Sensitisation. http://www.oecd-ilibrary.org/environment/test-no-442c-in-chemico-skin-sensitisation_9789264229709-en (Accessed on 10 Jun. 2015), OECD Publishing.
(20) Urbisch, D., Mehling. A., Guth. K., Ramirez, T., Honarvar, N., Kolle, S., Landsiedel, R., Jaworska, J., Kern. P. S., Gerberick. F., Natsch. A., Emter, R., Ashikaga, T., Miyazawa. M., and Sakaguchi. H. (2015)

Assessing skin sensitization hazard in mice and men using non-animal test methods. *Regul. Toxicol. Pharmacol.* 71, 337-351.

(21) Python, F., Goebel, C., and Aeby, P. (2007) Assessment of the U937 cell line for the detection of contact allergens. *Toxicol. Appl. Pharmacol.* 220, 113-124.

(22) Ashikaga, T., Yoshida, Y., Hirota, M., Yoneyama, K., Itagaki. H., Sakaguchi. H., Miyazawa. M., Ito, Y., Suzuki, Hi., and Toyoda, H. (2006) Development of an in vitro skin sensitization test using human cell lines: the human Cell Line Activation Test (h-CLAT). 1. Optimization of the h-CLAT protocol. Toxicol. In Vitro 20, 767-773.

(23) Merckel, F., Bernard, G., Mutschler, J., Gimenez-Arnau, E., Gerberick. G. F., and Lepoittevin, J. P. (2010) Effect of a microemulsion system on hapten-peptide reactivity studies: examples of hydroxycitronellal and citral, fragrance skin sensitizers, with glutathione. *Chem. Res. Toxicol.* 23, 1433-1441.

(24) Gerberick, G. F., Troutman, J. A., Foertsch, L. M., Vassallo, J, D., Quijano. M., Dobson, R. L., Goebel, C., and Lepoittevin, J. P. (2009) Investigation of peptide reactivity of pro-hapten skin sensitizers using a peroxidase-peroxide oxidation system. *Toxicol. Sci.* 112, 164-174.

(25) Karlberg. A. T., Bergstrom, M. A., Borje, A., Luthman, K., and Nilsson, J. L. (2008) Allergic contact dermatitis-formation, structural requirements, and reactivity of skin sensitizers. *Chem. Res. Toxicol.* 21, 53-69.

(26) Divkovic, M., Pease, C. K., Gerberick, G. F., and Basketter, D. A. (2005) Hapten-protein binding: from theory to practical application in the in vitro prediction of skin sensitization. *Contact dermatitis* 53, 189-200.

(27) Smith Pease, C. K., Basketter, D. A., and Patlewicz, G. Y. (2003) Contact allergy: the role of skin chemistry and metabolism. *Clin. Exp. Dermatol.* 28, 177-183.

(28) Aptula. A., Patlewicz, G., and Roberts, D. (2005) Skin sensitization: reaction mechanistic applicability domains for structure-activity relationships. *Chem. Res. Toxicol.* 18, 1420-1426.

(29) Schultz, T., Rogers, K., and Aptula, A. (2009) Read-across to rank skin sensitization potential: subcategories for the Michael acceptor domain. *Contact dermatitis* 60, 21-31.

(30) Schultz. T., Yarbrough, J., Hunter, R., and Aptula, A. (2007) Verification of the structural alerts for Michael acceptors. *Chem. Res. Toxicol* 20, 1359-1363.

(31) Schultz, T., Yarbrough, J., and Johnson, E. (2005) Structure-activity relationships for reactivity of carbonyl-containing compounds with glutathione. *SAR QSAR Environ. Res.* 16, 313-322.

(32) Kligman, A. M. (1966) The identification of contact allergens by human assay. 3. The maximization test: a procedure for screening and rating contact sensitizers. *J. Invest. Dermatol* 47, 393-409.

(33) McNamee, P. M., Api, A. M., Basketter, D. A., Frank Gerberick, G., Gilpin, D. A., Hall, B. M., Jowsey, I., and Robinson, M. K. (2008) A review of critical factors in the conduct and interpretation of the human repeat insult patch test. *Regul. Toxicol. Pharmacol.* 52, 24-34.

(34) Nukada, Y., Ashikaga, T., Miyazawa, M., Hirota, M., Sakaguchi, H., Sasa, H., and Nishiyama. N. (2012) Prediction of skin sensitization potency of chemicals by human Cell Line Activation Test (h-CLAT) and an attempt at classifying skin sensitization potency. *Toxicol. In Vitro* 26, 1150-1160.

(35) Azam, P., Peiffer, J.-L., Chamousset, D., Tissier, M.-H., Bonnet, P.-A., Vian. L., Fabre, I., and Ourlin, J.-C. (2006) The cytokine-dependent MUTZ-3 cell line as an in vitro model for the screening of contact sensitizers. *Toxicol. Appl. Pharmacol.* 212, 14-23.

(36) Ade. N., Leon, F., Pallardy, M., Peiffer, J.-L., Kerdine-Romer. S., Tissier. M.-H., Bonnet, P.-A., Fabre, I., and Ourlin, J.-C. (2009) HMOX1 and NQO1 genes are upregulated in response to contact sensitizers in dendritic cells and THP-1 cell line: role of the Keap1/Nrf2 pathway. *Toxicol. Sci.* 107, 451-460.

(37) Natsch, A. (2010) The Nrf2-Keap1-ARE toxicity pathway as a cellular sensor for skin sensitizers-functional relevance and a hypothesis on innate reactions to skin sensitizers. *Toxicol. Sci.* 113, 284-292.

(38) Vandebriel, R., Pennings, J., Baken. K., Pronk, T., Boorsma, A., Gottschalk, R., and Van Loveren, H. (2010) Keratinocyte gene expression profiles discriminate sensitizing and irritating compounds. *Toxicol. Sci.* 117, 81-89.

(39) Gerberick, G., Vassallo. J., Foertsch, L., Price, B., Chancy, J., and Lepoittevin J.-P. (2007) Quantification of chemical peptide reactivity for screening contact allergens: a classification tree model approach. *Toxicol. Sci.* 97, 417-427.

(40) Roberts, D. W., and Natsch. A. (2009) High throughput kinetic profiling approach for covalent binding to peptides: application to skin sensitization potency of Michael acceptor electrophiles. *Chem. Res. Toxicol.* 22, 592-603.

(41) Fujita, M., Hioki, T., and Jinbo. Y. (2014) Reagents for detecting skin-sensitizing potential and method for determining the potential, In *Jpn. Kokai Tokkyo Koho* (2014), JP 2014037995A. p 13 pp., Fujifilm Corporation, Japan.

(42) Fujita. M., Yamamoto, Y., Tahara, H., Kasahara, T., Jimbo, Y., and Hioki. T. (2014) Development of a prediction method for skin sensitization using novel cysteine and lysine derivatives. *J. Pharmacol. Toxicol. Methods* 70, 94-105.

(43) Okamoto. M., and Takahashi, K. (2009) Chemical substance sensitizing-potential verification method using fluorescent cysteine derivative, and fluorescent cysteine derivative, In *Jpn. Kokai Tokkyo Koho* (2009). JP 2009222466 A p 17 pp., Sumitomo Chemical Co., Ltd., Japan.

(44) Chipinda, I., Ajibola, R., Morakinyo, M., Ruwona, T., Simoyi, R., and Siegel. P. (2010) Rapid and simple kinetics screening assay for electrophilic dermal sensitizers using nitrobenzenethiol. *Chem. Res. Toxicol.* 23, 918-925.

(45) Roberts, D. W., and Aptula. A. O. (2014) Electrophilic Reactivity and Skin Sensitization Potency of SNAr Electrophiles. *Chem. Res. Toxicol.* 27, 240-246.

(46) Roberts, D., and Natsch. A. (2009) High throughput kinetic profiling approach for covalent binding to peptides: application to skin sensitization potency of Michael acceptor electrophiles. *Chem. Res. Toxicol.* 22, 592-603.

(47) Andres. E., Sa-Rocha, V. M., Barrichello, C., Haupt. T., Ellis, G., and Natsch, A. (2013) The sensitivity of the KeratinoSens assay to evaluate plant extracts: a pilot study. *Toxicol. In Vitro* 27, 1220-1225.

(48) Natsch, A., Gfeller, H., Rothaupt, M., and Ellis, G. (2007) Utility and limitations of a peptide reactivity assay to predict fragrance allergens in vitro. *Toxicol. In Vitro* 21, 1220-1226.

(49) Schwöbel, J., Koleva, Y., Enoch, S., Bajot. F., Hewitt, M., Madden, J., Roberts, D., Schultz, T., and Cronin, M. (2011) Measurement and estimation of electrophilic reactivity for predictive toxicology. *Chem. Rev.* 111, 2562-2596.

(50) Rosenker, C., Krenskee, E., Houk. K., and Wipf, P. (2013) Influence of base and structure in the reversible covalent conjugate addition of thiol to polycyclic enone scaffolds. *Org. Lett.* 15, 1076-1079.
(51) Böhme, A., Thaens, D., Paschke. A., and Schüürmann, G. (2009) Kinetic glutathione chemoassay to quantify thiol reactivity of organic electrophiles—application to alpha,beta-unsaturated ketones, acrylates, and propiolates. *Chem. Res. Toxicol.* 22, 742-750.
(52) Emter, R., van der Veen, J. W., Adamson, G., Ezendam. J., Loveren, H. V., and Natsch. A. (2013) Gene expression changes induced by skin sensitizers in the KeratinoSens cell line: Discriminating Nrf2-dependent and Nrf2-independent events. *Toxicol. In Vitro* 27, 2225-2232.
(53) Patlewicz, G., Basketter, D., Smith. C., Hotchkiss, S., and Roberts, D. (2001) Skin-sensitization structure-activity relationships for aldehydes. *Contact dermatitis* 44, 331-336.
(54) Roberts, D., and Aptula, A. (2009) Does the extreme skin sensitization potency of benzoquinone result from special chemistry? *Contact dermatitis* 61, 332-336.
(55) Payton. F., Sandusky, P., and Alwornh, W. L. (2007) NMR study of the solution structure of curcumin. *J. Nat. Prod.* 70, 143-146.
(56) Jovanovic, S. V., Steenken, S., Boone. C. W., and Simic. M. G. (1999) H-Atom Transfer Is A Preferred Antioxidant Mechanism of Curcumin. *J. Am. Chem. Soc.* 121, 9677-9681.
(57) Grant, K. L., and Schneider, C, D. (2000) Turmeric. *Am. J. Health Syst. Pharm.* 57, 1121-1122.
(58) Vocanson. M., Valeyrie, M., Rozieres, A., Hennino. A., Floc'h. F., Gard, A., and Nicolas, J. F. (2007) Lack of evidence for allergenic properties of coumarin in a fragrance allergy mouse model. *Contact dermatitis* 57, 361-364.
(59) Kanerva, L., Estlander, T., and Jolanki, R. (1988) Sensitization to patch test acrylates. *Contact dermatitis* 18, 10-15.
(60) Enoch, S., and Roberts, D. (2013) Predicting skin sensitization potency for Michael acceptors in the LLNA using quantum mechanics calculations. *Chem. Res. Toxicol.* 26, 767-774.
(61) Patlewicz, G., Roberts, D. W., and Uriarte, E. (2008) A comparison of reactivity schemes for the prediction skin sensitization potential. *Chem. Res. Toxicol.* 21, 521-541.
(62) Nukada, Y., Miyazawa. M., Kazutoshi, S., Sakaguchi. H., and Nishiyama, N. (2013) Data integration of non-animal tests for the development of a test battery to predict the skin sensitizing potential and potency of chemicals. *Toxicol. In Vitro* 27, 609-618.
(63) Chan, K., Poon, R., and O'Brien. P. J. (2008) Application of structure-activity relationships to investigate the molecular mechanisms of hepatocyte toxicity and electrophilic reactivity of alpha,beta-unsaturated aldehydes. *J. Appl. Toxicol.* 28, 1027-1039.
(64) Natsch, A., Ryan, C. A., Foertsch, L., Emter, R., Jaworska, J., Gerberick, F., and Kern, P. (2013) A dataset on 145 chemicals tested in alternative assays for skin sensitization undergoing prevalidation. *J Appl. Toxicol.* 33, 1337-1352.
(65) Mitchell, J. C., and Dupuis, G. (1971) Allergic contact dermatitis from sesquiterpenoids of the Compositae family of plants. *Br. J. Dermatol.* 84, 139-150.
(66) Jacob, M., Brinkmann, J., and Schmidt, T. (2012) Sesquiterpene lactone mix as a diagnostic tool for Asteraceae allergic contact dermatitis: chemical explanation for its poor performance and Sesquiterpene lactone mix II as a proposed improvement. *Contact dermatitis* 66, 233-240.
(67) Paulsen, E., Andersen, K. E., and Hanusen, B. M. (2001) An 8-year experience with routine SL mix patch testing supplemented with Compositae mix in Denmark. *Contact dermatitis* 45, 29-35.
(68) Hausen, B. M. (1981) Occupational contact allergy to feverfew *Tanacetum parthenium* (L.) Schultz-Bip.; Asteraceae. *Dermatosen Beruf Umwelt* 29, 18-21.
(69) Avonto, C., Taglialatela-Scafati, O., Pollastro, F., Minassi, A., Di Marzo, V., De Petrocellis, L., and Appendino, G. (2011) An NMR spectroscopic method to identify and classify thiol-trapping agents: revival of Michael acceptors for drug discovery? *Angew. Chem. Int. Ed. Engl.* 50, 467-471.
(70) Kern. P. S., Gerberick, G. F., Ryan, C. A., Kimber, I., Aptula, A., and Basketter, D. A. (2010) Local lymph node data for the evaluation of skin sensitization alternatives: a second compilation. *Dermatitis* 21, 8-32.
(71) Natsch, A., Haupt, T., and Laue, H. (2011) Relating skin sensitizing potency to chemical reactivity: reactive Michael acceptors inhibit NF-kappaB signaling and are less sensitizing than S(N)Ar— and S(N)2-reactive chemicals. *Chem. Res. Toxicol.* 24, 2018-2027.
(72) Bos, J., and Meinardi, M. (2000) The 500 Dalton rule for the skin penetration of chemical compounds and drugs. *Exp. Dermatol.* 9, 165-169.
(73) Niklasson. I. B., Ponting, D. J., Luthman. K., and Karlberg. A.-T. (2014) Bioactivation of cinnamic alcohol forms several strong skin sensitizers. *Chem. Res. Toxicol.* 27, 568-575.
(74) Lalko, J. F., Dearman, R. J., Gerberick. G. F., Troutman, J. A., Api, A. M., and Kimber, I. (2013) Reactivity of chemical respiratory allergens in the Peroxidase Peptide Reactivity Assay. *Toxicol. In Vitro* 27, 651-661.
(75) Helaskoski, E., Kuuliala, O., and Aalto-Korte. K. (2009) Occupational contact urticaria caused by cyclic acid anhydrides. *Contact dermatitis* 60, 214-221.
(76) Hausen. B. M., Breuer, J., Weglewski, J., and Ruecker, G. (1991) α-Peroxyachifolid and other new sensitizing sesquiterpene lactones from yarrow (*Achillea millefolium* L., Compositae). *Contact Dermatitis* 24, 274-280.
(77) Paulsen, E., Andersen, K. E., and Hausen, B. M. (2001) Sensitization and cross-reaction patterns in Danish Compositae-allergic patients. *Contact dermatitis* 45, 197-204.
(78) el-Feraly, F. S., and Chan, Y. M. (1978) Isolation and characterization of the sesquiterpene lactones costunolide, parthenolide, costunolide diepoxide, santamarine, and reynosin from *Magnolia grandiflora* L. *J. Pharm. Sci.* 67, 347-350.
(79) Avula, B., Wang. Y.-H., Wang, M., Avonto. C., Zhao, J., Smillie, T. J., Rua, D., and Khan, I. A. (2014) Quantitative determination of phenolic compounds by UHPLC-UV-MS and use of partial least-square discriminant analysis to differentiate chemo-types of Chamomile/*Chrysanthemum* flower heads. *J. Pharm. Biomed. Anal.* 88, 278-288.
(80) Samek. Z., Holub, M., Grabarczyk, H., Drozdz, B., and Herout, V. (1977) Terpenes. CCXXXVI. The structure of hydroxyisonobilin, a cytostatically active sesquiterpenic lactone from the leaves of *Anthemis nobilis*. *Collect. Czech. Chem. Commun.* 42, 1065-1068.

INCORPORATIONS BY REFERENCES

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A spectrophotometric method of detecting skin sensitization potential of at least one chemical compound, comprising
    mixing at least one of a fluorescent, a luminescent, a colored and a UV-absorbing nucleophile with at least one chemical compound to form a mixture comprising at least one conjugate;
    removing an amount of unreacted nucleophile from the mixture;
    quantifying the absorbance of the at least one conjugate using a spectrophotometer;
    determining the skin sensitization potential of the at least one chemical compound by comparing the absorbance of at least one conjugate with a reference absorbance; and
    identifying at least one chemical compound as a sensitizing compound when there is a measurable difference between the absorbance of the conjugate and the absorbance of the reference.

2. The method of claim 1, wherein the spectrophotometer is a multidetection microplate reader.

3. The method of claim 1, wherein the absorbance is measured at wavelength ranging from about 200 nm to about 780 nm.

4. The method of claim 1, wherein the step of mixing a nucleophile with at least one chemical compound further comprising adding a base.

5. The method of claim 1, wherein the base concentration is about 1% to about 50% of the nucleophile concentration.

6. The method of claim 1, wherein the nucleophile comprises an aromatic-thiol, an aliphatic-thiol, an alcohol, or an amine.

7. The method of claim 1, wherein the chemical compound is contained in an extract derived from a natural material.

8. The method of claim 1, wherein the chemical compound is contained in a mixture of chemical compounds.

9. The method of claim 1, wherein the chemical compound is contained in a mixture of chemical compounds formed by metabolic activation.

10. A method for measuring the skin sensitization potential of a chemical compound, comprising the steps of:
    (a) mixing a model nucleophile with the chemical compound;
        determining a reaction response of the chemical compound after mixing with the model nucleophile;
        identifying the difference between a spectroscopic response of the chemical compound after the reaction and a reference response;
        calculating the degree of reaction of the chemical compound by comparing the reaction response with a reference response; and
        identifying the chemical as a sensitizing compound based on the difference between the reaction response and the reference response; or
    (b) mixing a model nucleophile with the chemical compound;
        acquiring a spectrum of the chemical compound using NMR spectroscopy;
        determining a degree of reaction for the chemical compound by comparing a peak area of the spectrum of the chemical compound with a peak area of a reference spectrum;
        determining the difference between the peak area of the spectrum of the chemical compound and the peak area of the reference spectrum; and
        identifying the chemical compound as a sensitizing compound based on the difference between the peak area of the spectrum of the chemical compound and the peak area of the reference spectrum;
    (c) mixing at least one of a fluorescent, a luminescent, a colored, and a UV-absorbing nucleophile with the chemical compound to form a mixture comprising an adduct;
        removing an amount of unreacted nucleophile from the mixture by using a selective scavenger;
        quantifying the spectrophotometric response of the adduct using a spectrophotometer;
        determining the skin sensitization potential of the compound by comparing the response of the adduct with a reference response; and
        identifying the chemical compound as a sensitizing compound when there is a measurable difference between the response of the adduct and the response of the reference.

11. The method of claim 10, wherein the spectrophotometer is a microplate photometer.

12. The method of claim 10, wherein the response is measured at wavelength ranging from about 200 nm to about 780 nm.

13. The method of claim 10, wherein the step of mixing a nucleophile with at least one chemical compound further comprising adding a catalyst.

14. The method of claim 10, wherein the catalyst concentration is about 1% to about 50% of the model nucleophile concentration.

15. The method of claim 10, wherein the nucleophile comprises an aromatic/aliphatic-thiol, -alcohol, or -amine.

16. The method of claim 10, wherein the nucleophile comprises xanthyl, cyaninyl, napthyl, dansyl, coumaryl, oxadiazolyl, anthracyl, pyrenyl, oxaziyl, acridinyl, flavanyl, arylmethinyl, or tetrapyrrolinyl.

17. The method of claim 10, wherein the chemical sensitizer comprises a electrophile.

18. The method of claim 10, wherein the test chemical compound comprises a natural product whole extract, a natural product enriched fraction, a single natural product, a mixture of components derived from botanicals, an essential oil, a mixture of components derived from aged essential oil or a mixture of components derived from fresh plant material, a mixture of components derived from perfume, a mixture of components derived from personal care products, a mixture of components derived from aromatherapy, a mixture of components derived from a hair care product, a single synthetic chemical, a mixture of synthetic chemicals, a mixture of components derived from a synthetic chemical, a mixture of components derived from chemical activation or reactive intermediates.

19. The method of claim 10, wherein the test chemical compound comprises a mixture of components) derived upon biotic or abiotic activation, a mixture of component(s) derived upon prokaryotic or eukaryotic metabolism, a mixture of component(s) derived from exogenous transformation including xenobiotic metabolism, a mixture of component(s) derived from genetically modified organism a mixture of components) derived upon activation with oxidative stress inducers, a mixture of component upon metabolic activation or a mixture of component upon enzymatic activation.

* * * * *